US011725065B2

(12) United States Patent
Giese et al.

(10) Patent No.: US 11,725,065 B2
(45) Date of Patent: *Aug. 15, 2023

(54) ASSEMBLY OF BISPECIFIC ANTIBODIES

(71) Applicant: Genentech, Inc., South San Francisco, CA (US)

(72) Inventors: Glen Giese, Belmont, CA (US); Amy Lim, Palo Alto, CA (US); Josefine Persson, Half Moon Bay, CA (US); Justin Scheer, Half Moon Bay, CA (US); Ambrose Williams, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 16/820,660

(22) Filed: Mar. 16, 2020

(65) Prior Publication Data

US 2020/0317820 A1    Oct. 8, 2020

Related U.S. Application Data

(60) Continuation of application No. 15/789,775, filed on Oct. 20, 2017, now Pat. No. 10,626,189, which is a division of application No. 14/251,428, filed as application No. PCT/US2012/059810 on Oct. 11, 2012, now Pat. No. 9,862,778.

(60) Provisional application No. 61/545,863, filed on Oct. 11, 2011, provisional application No. 61/546,503, filed on Oct. 12, 2011, provisional application No. 61/560,704, filed on Nov. 16, 2011, provisional application No. 61/676,837, filed on Jul. 27, 2012.

(51) Int. Cl.
*C07K 16/46* (2006.01)

(52) U.S. Cl.
CPC ........ *C07K 16/468* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2317/622* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley |
| 4,560,655 A | 12/1985 | Baker |
| 4,601,978 A | 7/1986 | Karin |
| 4,657,866 A | 4/1987 | Kumar |
| 4,767,704 A | 8/1988 | Cleveland et al. |
| 4,816,567 A | 3/1989 | Cabilly |
| 4,927,762 A | 5/1990 | Darfler |
| 5,122,469 A | 6/1992 | Mather |
| 5,143,844 A | 9/1992 | Abrahmsen |
| 5,264,365 A | 11/1993 | Georgiou |
| 5,508,192 A | 4/1996 | Georgiou |
| 5,523,210 A | 6/1996 | Paulus |
| 5,591,828 A | 1/1997 | Bosslet |
| 5,641,870 A | 6/1997 | Rinderknecht |
| 5,731,168 A | 3/1998 | Carter |
| 5,789,229 A | 8/1998 | Wertz |
| 5,807,706 A | 9/1998 | Carter |
| 6,027,888 A | 2/2000 | Georgiou |
| 6,083,715 A | 7/2000 | Georgiou |
| 6,534,628 B1 | 3/2003 | Nilsson |
| 6,660,843 B1 | 12/2003 | Feige |
| 7,612,181 B2 | 11/2009 | Wu |
| 7,642,228 B2 | 1/2010 | Carter |
| 7,714,111 B2 | 5/2010 | Sun |
| 8,350,013 B2 | 1/2013 | Sun |
| 9,150,663 B2 | 10/2015 | Labrijn |
| 9,862,778 B2 * | 1/2018 | Giese .................. C07K 16/468 |
| 10,626,189 B2 * | 4/2020 | Giese .................. C07K 16/468 |
| 2002/0004587 A1 | 1/2002 | Miller |
| 2003/0078385 A1 | 4/2003 | Arathoon |
| 2003/0176352 A1 | 9/2003 | Min |
| 2003/0195156 A1 | 10/2003 | Min |
| 2003/0229023 A1 | 12/2003 | Oliner |
| 2003/0236193 A1 | 12/2003 | Oliner |
| 2004/0191243 A1 | 9/2004 | Chen |
| 2004/0197324 A1 | 10/2004 | Liu |

(Continued)

FOREIGN PATENT DOCUMENTS

| | | |
|---|---|---|
| CN | 1478903 A | 3/2004 |
| CN | 1759186 A | 4/2006 |

(Continued)

OTHER PUBLICATIONS

Williams et al., Biotechnology Progress 31(5): 1315-1322 (Year: 2015).*
Arakawa, T. et al. (2004, epub. May 20, 2004). "Elution of Antibodies From a Protein-A Column by Aqueous Arginine Solutions," Protein Expression and Purification 36:244-248.
Arie, J-P. et al. (Jan. 1, 2001). "Chaperone Function of FkpA, A Heat Shock Prolyl Isomerase, in the Periplasm of *Escherichia coli*," Molecular Micorbiology 39(1):199-210.
Barnes, D. et al. (Mar. 1, 1980). "Methods for Growth of Cultured Cells in Serum-Free Medium," Anal. Biochem. 102(2):255-270.
Bass, S. et al. (1990) "Hormone Phage: An Enrichment Method for Variant Proteins with Altered Binding Properties," Proteins: Structure, Function, and Genetics 8:309-314.

(Continued)

*Primary Examiner* — Phuong Huynh
(74) *Attorney, Agent, or Firm* — Morrison & Foerster LLP

(57) ABSTRACT

Described herein are methods for the efficient production of a heteromultimeric protein, such as a bispecific antibody. Heteromultimeric proteins may be capable of specifically binding to more than one target molecule or different epitopes on a single target molecule. The methods modulate parameters to improve assembly of the heteromultimeric proteins at higher yield and efficiency than otherwise possible. Also described are compositions comprising a hinge-containing polypeptide, such as a half-antibody.

20 Claims, 14 Drawing Sheets

(56) References Cited

U.S. PATENT DOCUMENTS

| | | |
|---|---|---|
| 2007/0178552 A1 | 8/2007 | Arathoon |
| 2007/0274985 A1 | 11/2007 | Dubel |
| 2008/0064831 A1 | 3/2008 | Chervakov |
| 2009/0182127 A1 | 7/2009 | Kjaergaard |
| 2010/0105874 A1 | 4/2010 | Schuurman |
| 2011/0054151 A1 | 3/2011 | Lazar |
| 2011/0243966 A1 | 10/2011 | Farrington |
| 2011/0287009 A1 | 11/2011 | Scheer |
| 2012/0259099 A1 | 10/2012 | Choe |
| 2012/0283416 A1 | 11/2012 | Frauenschuh |
| 2012/0302737 A1 | 11/2012 | Christensen |
| 2018/0162955 A1 | 6/2018 | Giese |

FOREIGN PATENT DOCUMENTS

| | | | |
|---|---|---|---|
| CN | 200180215 A | 8/2010 | |
| JP | H276899 A | 3/1990 | |
| JP | H06090786 A | 4/1994 | |
| JP | 2007524602 A | 8/2007 | |
| JP | 2008511337 A | 4/2008 | |
| JP | 2009541275 A | 11/2009 | |
| JP | 2010522701 A | 7/2010 | |
| JP | 2010528993 A | 8/2010 | |
| RU | 2203319 C2 | 4/2003 | |
| WO | WO1987000195 A1 | 1/1987 | |
| WO | WO1990003430 A1 | 4/1990 | |
| WO | WO1993011161 A1 | 6/1993 | |
| WO | WO1996027011 A1 | 9/1996 | |
| WO | WO1998050431 A2 | 11/1998 | |
| WO | WO1998050431 A3 | 11/1998 | |
| WO | WO200024770 A2 | 5/2000 | |
| WO | WO200029004 A1 | 5/2000 | |
| WO | WO200024770 A3 | 9/2000 | |
| WO | WO200024770 A9 | 10/2000 | |
| WO | WO2002051870 A2 | 7/2002 | |
| WO | WO2002051870 A3 | 4/2003 | |
| WO | WO2003035694 A2 | 5/2003 | |
| WO | WO2003057134 A2 | 7/2003 | |
| WO | WO2003035694 A3 | 10/2003 | |
| WO | WO2004009618 A2 | 1/2004 | |
| WO | WO2004026329 A1 | 4/2004 | |
| WO | WO2004091658 A1 | 10/2004 | |
| WO | WO2004092393 A1 | 10/2004 | |
| WO | WO2005035572 A2 | 4/2005 | |
| WO | WO2006028936 A2 | 3/2006 | |
| WO | WO2006028956 A2 | 3/2006 | |
| WO | WO2006028936 A3 | 9/2006 | |
| WO | WO2005035572 A3 | 1/2007 | |
| WO | WO2007147901 A1 | 12/2007 | |
| WO | WO2008119353 A1 | 10/2008 | |
| WO | WO2008145142 A1 | 12/2008 | |
| WO | WO2009089004 A1 | 7/2009 | |
| WO | WO2010034605 A1 | 4/2010 | |
| WO | WO2011073389 A1 | 6/2011 | |
| WO | WO2011074717 A1 | 6/2011 | |
| WO | WO2011133886 A2 | 10/2011 | |
| WO | WO2011143545 A1 | 11/2011 | |
| WO | WO2011133886 A3 | 12/2011 | |
| WO | WO-2013055958 A1 * | 4/2013 | ............... C07K 1/36 |

OTHER PUBLICATIONS

Berg, J. et al. (Jun. 1991). "Bispecific antibodies that mediate killing of cells infected with human immunodeficiency virus of any strain" P. Natl. Acad. Sci. USA 88:4723-4727.

Bostrom, J. et al. (Mar. 2009). "Variants of the Antibody Herceptin that Interact with HER2 and VEGF at the Antigen Binding Site" Science 323:1610-1614.

Bothmann, H. et al., (Jun. 2, 2000). "The Periplasmic *Escherichia coli* Peptidylprolyl cis,trans-Isomerase FkpA" The Journal of Biological Chemistry 275(22):17100-17105.

Burton, D.R. (1985). "Immunoglobulin G: Functional sites," Moiec. Immunol. 22(3):161-206.

Carlring, J. et al. (Jul. 21, 2011). "A Novel Redox Method for Rapid Production of Functional Bi-Specific Antibodies for Use in Early Pilot Studies," Plos One 6(7)(e 22533):1-7.

Chamow, S.M et al. (1995), "A Humanized, Bispecific Immunoadhesin-Antibody that Retargets CD3+ Effectors to Kill HIV-1-Infected Cells" J Hematotherapy 4:439-446.

Chen, J. et al. (Jul. 9, 1999). "Chaperone activity of DsbC*," The Journal of Biological Chemistry 274 (28):19601-19605.

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Chothia, C. et al. (Aug. 20, 1987). "Canonical Structures for the Hypervariable Regions of Immunoglobulins," J. Mol. Biol. 196(4):901-917.

Davies, J. et al. (Feb. 21, 1994). "'Camelising' Human Antibody Fragments: NMR Studies on VH Domains," FEBS Letters 339(3):285-290.

Dooley, H. et al. (2006, e-pub. Jul. 22, 2005). "Antibody Repertoire Development in Cartilaginous Fish," Dev. Comp. Immunol. 30:43-56.

Ejima, D. et al. (2005, e-pub. Jul. 26, 2005). "Effective Elution of Antibodies by Arginine and Arginine Derivatives in Affinity Column Chromatography," Analytical Biochemistry 345:250-257.

Ellman, J. et al. (1991). "Biosynthetic Method for Introducing Unnatural Amino Acids Site-Specificaliy into Proteins," Meth. Enzym. 202:301-336.

Fischer, N. et al. (2007). "Bispecific Antibodies: Molecules that Enable Novel Therapeutic Strategies," Pathobiology 74:3-14.

Gombotz, W.R. et al. (May 1994). "The Stabilization of a Human IgM Monoclonal Antibody With Poly (Vinylpyrrolidone)," Pharm. Res. 11(5): 624-632.

Graham, F.L. et al. (1977). "Characteristics of a Human Cell Line Transformed by DNA from Human Adenovirus Type 5," J. Gen Virol. 36:59-72.

Grönwall C. et al. (Jun. 2008). "Generation of Affibody Ligands Binding Interleukin-2 Receptor α/CD25," Biotechnol. Appl. Biochem. 50(Pt. 2):97-112.

Guss, B. et al. (Jul. 1986). "Structure of the IgG-Binding Regions of Streptococcal Protein G," EMBO J. 5(7):1567-1575.

Ham, R.G. et al. (1979). "Media and Growth Requirements," Meth. Enzymol. 58:44-93.

Hamers-Casterman, C. et al. (Jun. 3, 1993). "Naturally Occurring Antibodies Devoid of Light Chains," Nature 363 (6428):446-448.

Hara, H. et al. (1996) "Overproduction of Penicillin-Binding Protein 7 Suppresses Thermosensitive Growth Defect at Low Osmolarity Due to an Spr Mutation of *Escherichia coli*," Microhial Drug Resistance 2(1):63-72.

Hollinger, P. et al. (Jul. 1993). ""Diabodies": Small Bivalent and Bispecific Antibody Fragments," Proc. Natl. Acad. Sci. Usa 90:6444-6448.

Holt, L. et al. (Nov. 2003) "Domain Antibodies: Proteins for Therapy," TRENDS in Biotechnology 21(11):484-490.

International Search Report dated Mar. 18, 2013, for PCT Application No. PCT/US2012/059810, filed on Oct. 11, 2012, 8 pages.

Jackman, J. et al., (Jul. 2, 2010), "Development of a Two-part Strategy to Identify a Therapeutic Human Bispedfic Antibody That Inhibits IgE Receptor Signaling," The Journal of Biological Chemistry 285(27):20850-20859.

Jiang, Y. et al. (Apr. 7, 2006). "Polyvinylpyrrolidone 40 Assists the Refolding of Bovine Carbonic Anhydrase B by Accelerating the Refolding of the First Molten Globule Intermediate," J. Biol. Chem. 281(16): 9058-9065.

Jin, H. et al. (Jun. 1, 2008). "MetMAb, the One-Armed 5D5 Anti-c-Met Antibody, Inhibits Orthotopic Pancreatic Tumor Growth and Improves Survival," Cancer Res 68:4360-4368.

Johnson, G. et al. (2003), "The Kabat Database and a Bioinformatics Example," Chapter 2 in Methods in Molecular Biology, Lo, B.K.C, Humana Press, Totawa, N.J., 248:11-25.

Joly, J.C. et al. (Mar. 1998). "Overexpression of *Escherichia coli* Oxidoreductases Increases Recombinant Insulin-like Growth Factor-I Accumulation," Proc. Natl. Acad. Sci. USA 95:2773-2777.

(56) References Cited

OTHER PUBLICATIONS

Jones, P.T. et al. (May 29, 1986). "Replacing the Complementarity-Determining Regions in a Human Antibody with Those From a Mouse" Nature 321:522-525.
Kikuchi, Y. et al. (1981). "The Nucleotide Sequence of the Promoter and the Amino-Terminal Region of Alkaline Phosphatase Structural Gene (phoA) of *Escherichia coli*," Nucleic Acids Res. 9(21):5671-5678.
Kontermann, R.E. (Jan. 2005). "Recombinant Bispecific Antibodies for Cancer Therapy," Acta Pharacol. Sinc. 26(1):1-9.
Lee, C.H. et al. (Oct. 1983). "Characterization of the Gene Encoding Heat-Stable Toxin II and Preliminary Molecular Epidemiological Studies of Enterotoxigenic *Escherichia coli* Heat-Stable Toxin II Producers," Infect. Immun. 42:264-268.
Lindmark, R. et al. (1983). "Binding of Immunoglobulins to Protein A and Immunoglobulin Levels in Mammalian Sera," J. Immunol. Meth. 62:1-13.
Liu, H. et al. (Jul. 2008). "Heterogeneity of Monoclonal Antibodies," J. of Pharmaceutical Sci. 97(7):2426-2447.
Lucas, B.K. et al. (1996). "High-Level Production of Recombinant Proteins in CHO Cells Using a Dicistronic DHFR Intron Expression Vector," Nucl. Acids Res. 24(9):1774-1779.
Malmborg, A.-C. et al. (1995). "BIAcore as a Tool in Antibody Engineering," J. Immunol. Methods 183:7-13.
Martens, T. et al. (Oct. 15, 2006). "A Novel One-Armed Anti-c-Met Antibody Inhibits Glioblastoma Growth In vivo," Clin. Cancer Res. 12(20):6144-6152.
Marvin, J.S. et al. (Jun. 2005). "Recombinant Approaches to IgG-Like Bispecific Antibodies," Acta Pharmacol, Sin. 26(6):649-658.
Mather, J.P. (Aug. 1980) "Establishment and Characterization of Two Distinct Mouse Testicular Epithelial Cell Lines," Biol. Reprod. 23(1):243-252.
Mather, J.P. et al. (1982) "Culture of Testicular Cells in Hormone-Supplemented Serum-Free Medium," Annals New York Academy of Sciences pp. 44-68.
Merchant, A. M. et al. (Jul. 1998). "An Efficient Route to Human Bispecific IgG," Nature Biotechnology 16:677-681.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Muyldermans, S. et al. (Apr. 2001). "Recognition of Antigens by Single-Domain Antibody Fragments: The Superfluous Luxury of Paired Domains," Trends Biochem. Sci. 26(4):230-235.
Nilsson, B. et al. (1987). "A Synthetic IgG-Binding Domain Based on Staphylococcal Protein A," Prot. Eng. 1:107-133.
Nord, K. et al. (1995). "A Combinatorial Library of an α-Helical Bacterial Receptor Domain," Prot. Eng. 8:601-608.
Nord, K. et al. (1997). "Binding Proteins Selected From Combinatorial Libraries of an α-Helical Bacterial Receptor Domain," Nat. Biotech. 15:772-777.
Noren, C.J. et al. (Apr. 14, 1989). "A General Method for Site-Specific Incorporation of Unnatural Amino Acids into Proteins," Science 244:182-188.
Orcutt, K.D. et al. (Apr. 2010, e-pub. Dec. 17, 2009). "A Modular IgG-scFv Bispecific Antibody Topology," Protein Engineering, Design & Selection 23(4):221-228.
Pack, P et al. (Nov. 1993). "Improved Bivalent Miniantibodies, With Identical Avidity as Whole Antibodies, Produced by High Cell Density Fermentation of *Escherichia coli*," Bio/Technology 11:1271-1277.
Pack, P. et al. (Feb. 18, 1992). "Miniantibodies: Use of Amphipathic Helices to Produce Functional, Flexibly-Linked Dimeric FV Fragments with High Avidity in *Escherichia coli*," Biochem. 31(6):1579-1584.
Picken, R.N. et al. (Oct. 1983). "Nucleotide Sequence of the Gene for Heat-Stable Enterotoxin II of *Escherichia coli*," Infect. Immun. 42(1):269-275.

Plückthun, A. (1994). "Antibodies From *Escherichia coli*," Chapter 11 in The Pharmacology of Monoclonal Antibodies, Rosenburg and Moore eds., Springer-Verlag, New York, N.Y., pp. 269-315.
Ponder, J.W. et al. (1987), "Tertiary Templates for Proteins Use of Packing Criteria in the Enumeration of Allowed Sequences for Different Structural Classes," J. Mol. Biol. 193:775-791.
Presta, L.G. (1992). "Antibody Engineering," Current Opinion in Structural Biology, 2:593-596.
Proba, K. et al. (1995). "Functional Antibody Single-chain Fragments From The Cytoplasm of *Escherichia coil* Influence of Thioredoxin Reductase (trxb)," Gene 159(2):203-207.
Ramm, K. et al. (2000). "The Periplasmic *Escherichia coli* Peptidyiprolyl cis,Trans-Isomerase FkpA," The Journal of Biological Chemistry 275(22):17106-17113.
Reyes, G.R., et al. (Jun. 17, 1982) "Expression of Human β-interferon cDNA Under the Control of a Thymidine Kinase Promoter from Herpes Simplex Virus," Nature 297:598-601.
Riechmann, L. et al. (Mar. 24, 1988). "Reshaping Human Antibodies for Therapy," Nature 332:323-327.
Ruppert, S. et al. (Mar. 11, 1993). "Cloning and Expression of Human TAFII250: a TBP-Associated Factor Implicated in Cell-Cycle Regulation," Nature 362:175-179.
Sanders, P.G. et al., (1984). "Amplification and Cloning of the Chinese hamster Glutamine Synthetase Gene," EMBO J. 3(1):65-71.
Sheriff, S. et al. (Sep. 1996). "Redefining the Minimal Antigen-Binding Fragment," Nature Struct. Biol. 3(9):733-736.
Shukla, A.A. et al. (2007). "Protein Aggregation Kinetics Druing Protein A Chromatography Case Study for an FC Fusion Protein," J. of Chromatography A 1171: 22-28.
Siebenlist, U. et al. (Jun. 1980). "*E. coli* RNA Polymerase Interacts Homologously With Two Different Promoters," Cell 20(2):269-281.
Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2): 133-147.
Simmons, L.C. et al. (May 1996). "Translational Level is a Critical Factor for the Secretion of Heterologous Proteins in *Escherichia coli*," Nat. Biotechnol. 14(5):629-634.
Tsumoto, K. et al. (2004, e-pub. May 20, 2004). "Role of Arginine in Protein Refolding, Solubilization, and Purification," Biotechnol. Prog. 20:1301-1308.
Tsumoto, K. et al. (2005). "Review: Why is Arginine Effective in Suppressing Agregation," Protein & Peptide Letters 12:613-619.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Der Neut Kolfschoten, M. et al. (Sep. 14, 2007). "Anti-Inflammatory Activity of Human IgG4 Antibodies by Dynamic Fab Arm Exchange," Science 317:1554-1557, retrieved from http://science.sciencemag.org/, last visited Jul. 21, 2017.
Ward, E.S. et al. (Oct. 1, 1989). "Binding Activities of a Repertoire of Single Immunoglobulin Variable Domains Secreted From *Escherichia coli*," Nature 341:544-546.
Williams, A.J. et al. (Sep. 1, 2015), "Improved Assembly of Bispecific Antibodies From Knob and Hole Half-Antibodies," Biotechnology Progress 31(5):1315-1322.
Written Opinion dated Mar. 18, 2013, for PCT Application No. PCT/US2012/059810, filed on Oct. 11, 2012, 8 pages.
Xu, J.L. et al. (Jul. 2000). "Diversity in the CDR3 Region of VH Is Sufficient for Most Antibody Specificities," Immunity 13:37-45.
Yaniv, M. (May 6, 1982). "Enhancing Elements for Activation of Eukaryotic Promoters," Nature 297:17-18.
Zapata, G. et al. (1995). "Engineering Linear F(ab')2 Fragments for Efficient Production in *Escherichia coli* and Enhanced Antiproliferative Activity," Protein Engineering 8(10):1057-1062.
Zhu, Z. et al. (1997). "Remodeling Domain Interfaces to Enhance Heterodimer Formation," Protein Science 6:781-788.

\* cited by examiner

ASSEMBLY OF BISPECIFIC ANTIBODIES

CROSS REFERENCE TO RELATED APPLICATIONS

This application is a continuation of divisional application Ser. No. 15/789,775, filed Oct. 20, 2017, now U.S. Pat. No. 10,626,189. issued Apr. 21, 2020 which is a divisional of U.S. non-provisional application Ser. No. 14/251,428 filed Apr. 11, 2014, now U.S. Pat. No. 9,862,778, issued Jan. 9, 2018, which is a continuation of International Application Number. PCT/US2012/059810 having an international filing date of Oct. 11, 2012. the entire contents of which are incorporated herein by reference, and which claims benefit under 35 U.S.C. § 119 to U.S. Provisional Application Nos. 61/545,863, filed on Oct. 11. 2011, 61/546,503, filed Oct. 12, 2011, 61/560,704, filed on Nov. 16, 2011 and 61/676,837, filed Jul. 27, 2012. The disclosure of each of the above-referenced Applications is incorporated herein by, reference in its entirety.

TECHNICAL FIELD

This disclosure relates to compositions and improved methods of assembling heteromultimeric proteins such as bispecific antibodies.

SEQUENCE LISTING

The instant application contains a Sequence Listing submitted via EFS-Web and hereby incorporated by reference in its entirety. Said ASCII copy, created on Apr. 11, 2014, is named P4764C1SeqList.txt, and is 770 bytes in size.

BACKGROUND

Monoclonal antibodies of the IgG type contain two identical antigen-binding arms and a constant domain (Fc). Antibodies with a differing specificity in their binding arms usually do not occur in nature and, therefore, have to be crafted with the help of chemical engineering (e.g., chemical cross-linking, etc.), recombinant DNA and/or cell-fusion technology.

Bispecific antibodies can bind simultaneously two different antigens. This property enables the development of therapeutic strategies that are not possible with conventional monoclonal antibodies. The large panel of imaginative bispecific antibody formats that has been developed reflects the strong interest for these molecules. See Berg J, Lotscher E, Steimer K S, et al., "Bispecific antibodies that mediate killing of cells infected with human immunodeficiency virus of any strain," Proc Natl Acad Sci USA (1991) 88(11): 4723-4727 and Fischer N and Leger O., "Biospecific Antibodies: Molecules That Enable Novel Therapeutic Strategies," Pathobiology (2007) 74:3-14.

Another class of multispecific molecules is recombinant fusion proteins. Recombinant fusion proteins consisting of the extracellular domain of immunoregulatory proteins and the constant (Fc) domain of immunoglobulin (Ig) represent a growing class of human therapeutics. Immunoadhesins combine the binding region of a protein sequence, with a desired specificity, with the effector domain of an antibody. Immunoadhesins have two important properties that are significant to their potential as therapeutic agents: the target specificity, and the pharmacokinetic stability (half-life in vivo that is comparable to that of antibodies). Immunoadhesins can be used as antagonist to inhibit or block deleterious interactions or as agonist to mimic or enhance physiological responses. See Chamow S M, Zhang D Z, Tan X Y, et al., "A humanized, bispecific immunoadhesin-antibody that retargets CD3+ effectors to kill HIV-1-infected cells," J Hematother 1995; 4(5): 439-446.

Other multispecific molecules have been discussed elsewhere. Examples include but are not limited to: Fisher et al., Pathobiology (2007) 74:3-14 (review of various bispecific formats); U.S. Pat. No. 6,660,843, issued Dec. 9, 2003 to Feige et al. (peptibodies); US Pat. Publ. No. 2002-004587 published Jan. 10, 2002 (multispecific antibodies); U.S. Pat. No. 7,612,181 issued Nov. 3, 2009 to Wu et al. (Dual Variable Domain format); U.S. Pat. No. 6,534,628, Nord K et al., Prot Eng (1995) 8:601-608, Nord K et al., Nat Biotech (1997) 15:772-777, and Gronwall et al., Biotechnol Appl Biochem. (2008) June; 50(Pt 2):97-112 (Affibodies); Martens et al., Clin Cancer Res (2006), 12: 6144-6152 and Jin et al., Cancer Res (2008) 68(11):4360-4368 (one armed antibodies); Bostrom et al., Science (2009) 323:1610-1614 (Dual Action Fab, aka mixed valency antibodies). Other formats are known to those skilled in the art.

The manufacturing of clinical grade material remains challenging for antibodies generally and especially for the multispecific molecules described above. As noted above, there are many paths to the production of molecules with mixed binding arms, i.e., binding arms that are not identical to each other. But each of these methods has its drawbacks.

Chemical cross-linking is labor intensive as the relevant species may yet need to be purified from homodimers and other undesirable by-products. In addition, the chemical modification steps can alter the integrity of the proteins thus leading to poor stability. Thus, this method is often inefficient and can lead to loss of antibody activity.

Cell-fusion technology (e.g., hybrid hybridomas) express two heavy and two light chains that assemble randomly leading to the generation of 10 antibody combinations. The desired heteromultimeric antibodies are only a small fraction of the antibodies thus produced. Purification of the desired heteromultimeric proteins dramatically reduces production yields and increases manufacturing costs.

Recombinant DNA techniques have been used to generate various heteromultimeric formats. e.g., single chain Fv, diabodies, etc., that do not comprise an Fc domain. A major drawback for this type of antibody molecule is the lack of the Fc domain and thus the ability of the antibody to trigger an effector function (e.g., complement activation, Fc-receptor binding etc.). Thus, a bispecific antibody comprising a functional Fc domain is desired.

Recombinant DNA techniques have also been used to generate 'knob into hole' bispecific antibodies. See US Patent Application 20030078385 (Arathoon et al.—Genentech). One constraint of this strategy is that the light chains of the two parent antibodies have to be identical to prevent mispairing and formation of undesired and/or inactive molecules when expressed in the same cell.

In addition, one of the limiting events during annealing and purification is the redox efficiency. Oxidized heterodimer typically only makes up 70-80% of the protein after this step (BioAnalyzer and MS-TOF). The remaining 20-30% of antibody is dimeric and lacks a covalent linkage (SEC-LLS). This can be removed but significantly impacts overall yields. Thus, there remains a need to improve the overall yield in antibody production, especially heterodimers. Described herein are methods that can improve overall yield of bispecific antibodies, heterodimers and the like. These and other aspects and advantages of the invention will be apparent from the description of the invention provided herein.

SUMMARY OF THE INVENTION

Production of heteromultimeric proteins assembled from two or more hinge-containing polypeptides, e.g., multispecific antibodies from two or more half-antibodies, using current techniques has drawbacks including the production of a mixture of products, reduced yield and decreased/elimination of effector function among others. In addition, aggregation and precipitation often occur during the preparation of each hinge-containing polypeptide and during the assembly or annealing of the heteromultimers. Aggregation and precipitation can greatly reduce the yield of the desired heteromultimer. Thus, it is desirable to produce heteromultimeric proteins more efficiently and at higher levels.

Disclosed herein are efficient production processes/methods for economical production of heteromultimeric proteins, e.g., multispecific antibodies, by using or modulating one or more of the following including without limitation: a stabilizer, a solubilizer, a reducing condition, selected pH and selected temperature, etc. The inventive methods described herein decreased loss of protein to precipitation and/or aggregation and improved the overall yield of heteromultimeric protein production, such as the production of bispecific antibodies.

In one aspect there is provided a method of forming or producing a heteromultimeric protein, said method comprising:
 a. Providing a first hinge-containing polypeptide at pH 4-9, preferably 5-9, in the presence of a first solubilizer, wherein the first hinge-containing polypeptide comprises a heteromultimerization domain;
 b. Providing a second hinge-containing polypeptide at pH 4-9, preferably 5-9, in the presence of a second solubilizer, wherein the second hinge-containing polypeptide comprises a heteromultimerization domain;
 c. Mixing the first and second hinge-containing polypeptides in a reducing condition to form an assembly mixture; and
 d. incubating the assembly mixture to form or produce a heteromultimeric protein comprising the first and second hinge-containing polypeptides, wherein the first hinge-containing polypeptide interacts with the second hinge-containing polypeptide at the heteromultimerization domain.

In certain embodiments of this aspect, step a and/or step b is preceded by the step of purifying the first and/or second hinge-containing polypeptide. In certain particular embodiments, the first and/or second hinge-containing polypeptide is purified by Protein A.

In another aspect there is provided a method of forming or producing a bispecific antibody, said method comprising:
 a. Providing a first half-antibody at pH 4-9, preferably 5-9, in the presence of a first solubilizer, wherein the first half-antibody comprises a heteromultimerization domain;
 b. Providing a second half-antibody at pH 4-9, preferably 5-9 in the presence of a second solubilizer, wherein the second half-antibody comprises a heteromultimerization domain;
 c. Mixing the first and second half-antibodies in a reducing condition to form an assembly mixture; and
 d. incubating the assembly mixture to form or produce a bispecific antibody comprising the first and second half-antibodies, wherein the first half-antibody interacts with the second half-antibody at the heteromultimerization domain.

In certain embodiments of this aspect, step a and/or step b is preceded by the step of purifying the first and/or second half-antibody. In certain particular embodiments, the first and/or second half-antibody is purified by Protein A.

In a further aspect there is provided a method of producing a heteromultimer, said method comprising providing an arginine containing mixture of hinge-containing polypeptides said mixture having a pH of between 4 and 9, preferably 5-9, adding a weak reductant and incubating under conditions so as to produce a heteromultimer.

In yet another aspect, there is provided a method of producing a heteromultimeric protein, said method comprising:
 a. Obtaining a protein A purified first hinge-containing polypeptide;
 b. Obtaining a protein A purified second hinge-containing polypeptide;
 c. Adjusting the pH of each half-antibody to between 4 and 9;
 d. Mixing the first and second hinge-containing polypeptide to obtain an assembly mixture,
 e. Adding a molar excess of a weak reductant to the assembly mixture; and
 f. incubating the assembly mixture to form a heteromultimeric protein comprising the first and second hinge-containing polypeptide.

In another aspect, there is provided a method of producing a heteromultimeric protein, said method comprising:
 a. Obtaining a protein A purified first hinge-containing polypeptide:
 b. Obtaining a protein A purified second hinge-containing polypeptide;
 c. Adjusting the pH of each hinge-containing polypeptide to between 4 and 9 in the presence of L-Arginine;
 d. Mixing the first and second hinge-containing polypeptide to obtain a mixed hinge-containing polypeptide pool, and
 e. incubating to form a heteromultimeric protein comprising the first and second hinge-containing polypeptide.

In certain embodiments of this aspect, the mixed hinge-containing polypeptide pool is incubated in a reducing condition. In certain embodiments, the hinge-containing polypeptide comprises a half-antibody, an immunoadhesin or a functional fragment thereof. In certain other embodiments, the Arginine is present at a concentration of 20 mM-1M, 20 mM to 200 mM, or 50 mM-200 mM. In certain other embodiments, PVP is added to the step d or step e. In certain embodiments, the pH is adjusted after mixing.

The instant applicants unexpectedly discovered that an intermediate pH hold of a hinge-containing polypeptide such as a half-antibody can promote conformation shift that enhanced subsequent assembly of the hinge-containing polypeptides. In certain embodiments, the intermediate pH is between pH 4 and 9, preferably 5 and 9, or at least pH 5, at least pH 5.5, at least pH 5.7, greater than pH 5, greater than pH 5.5, greater than pH 5.7, between 5 and 9, 5 and 8, 5.5 and 8, 5.5 and 9, 5.7 and 8, 5.7 and 9, 6 and 8, 6 and 9, 7 and 8, 7.5 and 8.5, or 7 and 8.5. A solubilizer can be added to prevent or minimize pH-induced precipitation of the hinge-containing polypeptide. In certain particular embodiments, the solubilizer is added before the intermediate pH hold. In certain embodiments, the first solubilizer and second solubilizer is each selected from the group consisting of arginine, histidine and sucrose, preferably arginine and/or histidine. In certain other embodiments, the arginine is an arginine salt and/or histidine is a histidine salt. In certain other embodiments, the arginine is an arginine derivative and/or histidine is a histidine derivative. In certain other embodiments, the arginine or histidine is L-arginine or L-histidine. In certain other embodiments, the arginine or histidine is arginine HCl or histidine HCl. In certain other embodiments, the arginine or histidine is arginine phosphate or histidine phosphate. In certain embodiments, the first and second solubilizers are different; while in other embodiments, the first and second solubilizers are the same. In certain preferred embodiments, both the first solubilizer and the second solubilizer comprise arginine. In yet other embodiments, the arginine is present at a concentration of between 20 mM to 1M, 20 mM to less than 1 M, 20 mM to 100 mM, 20 mM to 200 mM, 20 mM to 300 mM, 20 mM to 400 mM, 50 mM to 100 mM, 50 mM to 150 mM, 50 mM to 200 mM, 50 mM to 250 mM, or 50 mM to 300 mm, preferably 20 mM to 200 mM. In yet other embodiments, the solubilizer comprises an arginine derivative including without limitation acetyl-arginine. In other embodiments, both the first solubilizer and second solubilizer comprise histidine present at a concentration of between 20 mM to 1M, 20 mM to less than 1M, 20 mM to less than 500 mM, 20 mM to 100 mM, 20 mM to 200 mM, 20 mM to 300 mM, 20 mM to 400 mM, 50 mM to 100 mM, 50 mM to 150 mM, 50 mM to 200 mM. 50 mM to 250 mM, 50 mM to 300 mm, 50 mM to 400 mM, 50 mM to 500 mM, or 50 mM to 600 mM. In certain preferred embodiments, the solubilizer is added at a concentration of 50 mM. In certain other embodiments, the solubilizer is added at a concentration of 200 mM. In certain particular embodiments, arginine or histidine is added at a concentration of 20 mM, 50 mM, 100 mM, or 200 mM. In certain other particular embodiments, the first and/or second hinge-containing polypeptides are provided in the presence of both arginine and histidine. In other embodiments, the arginine and histidine are each present at a concentration of 20 mM to 1M, 20 mM to less than 1M, 20 mM to 100 mM, 20 mM to 200 mM, 20 mM to 300 mM, 20 mM to 400 mM, 50 mM to 100 mM, 50 mM to 150 mM, 50 mM to 200 mM, 50 mM to 250 mM, or 50 mM to 300 mM, preferably 50 mM to 200 mM.

In certain embodiments, the first and second hinge-containing polypeptides are mixed before the intermediate pH hold (i.e, pH adjustment). In certain other embodiments, the first and second hinge-containing polypeptides are mixed after the pH is adjusted in the first hinge-containing polypeptide and second hinge-containing polypeptide separately. In certain embodiments, a solubilizer is added before pH adjustment.

In certain embodiments, the first hinge-containing polypeptide and the second hinge-containing polypeptide are separately purified before mixing; while in other embodiments, the first hinge-containing polypeptide and the second hinge-containing polypeptide are co-purified after mixing. In certain particular embodiments, the hinge-containing polypeptide comprises a half-antibody. In certain embodiments, the assembled heteromultimeric protein can be subjected to further purification.

Any suitable methods can be used for purification including without limitation purification by protein A chromatography, protein G chromatography, hydrophobic interaction chromatography (HIC), fractionation on immunoaffinity column, ethanol precipitation, reverse phase chromatography on silica or on an ion-exchange resin such as DEAE, chromatofocusing, SDS-PAGE, ammonium sulfate precipitation, and gel filtration using, for example, Sephadex G-75, and other similar purification methods, and combinations thereof.

In certain embodiments, the hinge-containing polypeptide such as a half-antibody is purified by Protein A or Protein G chromatography. In another embodiment the first and second hinge-containing polypeptides are mixed prior to Protein A purification and co-purified over Protein A. In certain embodiments, the pH is adjusted after mixing the Protein A purified polypeptides. In other embodiments, the pH is adjusted prior to mixing the Protein A purified polypeptides. In certain embodiments, a solubilizer is added before pH adjustment.

In certain other embodiments, the hinge-containing polypeptide is purified by HIC or an ion-exchange column. It is within the ability of a person skilled in the art to select suitable purification methods. For example, the hinge-containing polypeptide can be purified by a Protein A column followed by an ion-exchange column; the hinge-containing polypeptide can also be purified by a Protein A column followed by a gel filtration column and/or HIC. In other examples, the hinge-containing polypeptide can be purified by one or more ion-exchange column before purification by a Protein A column. In certain embodiments, the washing and/or elution buffers used during any of the purification steps of the hinge-containing polypeptides do not contain arginine and/or histidine.

In yet other embodiments, the half-antibody eluted from the Protein A matrix or other column matrix at acidic pH is adjusted to an intermediate pH. This subsequent pH adjustment (also referred to as an intermediate pH hold) can cause precipitation of the hinge-containing polypeptide such as a half-antibody and thus lead to reduced yield of the assembled heteromultimeric protein. Thus, in certain embodiments, the half-antibody eluted from the Protein A or Protein G column at acidic pH is provided in the presence of a solubilizer before pH adjustment. In the event that a pH adjustment step is not necessary, in certain embodiments a solubilizer is preferably added to the purified hinge-containing polypeptide to prevent or reduce precipitation and/or aggregation.

In addition to intermediate pH hold, the instant applicants unexpectedly discovered that heating can enhance conformation shift and/or assembly of the hinge-containing polypeptides such as half-antibodies. Accordingly, in certain embodiments, one, more or all of the steps a-d of the inventive methods are heated at a temperature of between 15° C. and 39° C., 15° C. and 42° C., 18° C. and 37° C., 20° C. and 42° C., 20° C. and 25° C., 25° C. and 42° C., 25° C. and 35° C., 25° C. and 39° C., 30° C. and 35° C., 32° C. and 35° C. or 32° C. and 37° C., preferably 35° C. and 37° C., for at least 30 minutes. In certain embodiments, the incubation time is up to 72 hours, especially at room temperature. In some embodiments the incubation time is 3 hours at 35° C. In certain other embodiments, the temperature is at or about 30° C., 35° C., or 37° C.

Heating, however, can also increase aggregation and/or precipitation. Accordingly, in certain particular embodiments, a solubilizer is added to the half-antibody eluted from a Protein A or Protein G column before heating.

In certain embodiments, the hinge-containing polypeptide comprises a half-antibody, an immunoadhesin, or a functional fragment thereof. In certain particular embodiments, the hinge-containing polypeptide comprises an Fc component.

In certain particular embodiments, the first and/or second hinge-containing polypeptide comprises a half-antibody. In certain embodiments, the half-antibody is an IgG half-antibody. In certain particular embodiments, the IgG half-antibody is of the IgG1, IgG4 or IgG2 isotype. In certain advantageous embodiments, the signal peptide of the immunoglobulin molecule is retained to facilitate secretion of the half-antibody especially when produced in mammalian cells. In certain embodiments, the inventive method comprises providing a first and a second half-antibody, at pH 5-9 in the presence of arginine at a concentration of about 50 mM, and alternatively or additionally histidine at a concentration of about 200 mM. In certain embodiments, the first and/or second half-antibody each comprises an antigen binding domain specific for a different antigen or a different epitope on the same antigen and the assembled full antibody is a bispecific antibody. In certain other embodiments, the first and second half-antibodies are of the same isotype; while in other embodiments, the first and second half-antibody are of different isotypes.

The half-antibody may comprise a $V_L$ domain, a $V_H$ domain, a hinge domain, a $CH_2$ domain and/or a $CH_3$ domain. The half-antibody can also be a single chain polypeptide further comprising a tether, wherein said single chain polypeptide comprises domains positioned relative to each other in an N-terminal to C-terminal direction as follows: $V_L$-tether-$V_H$-hinge-$CH_2$-$CH_3$ In certain other embodiments, the half-antibody further comprises a $C_L$ domain and a $CH_1$ domain; and in further embodiments, the half-antibody can be a single chain polypeptide further comprising a tether, wherein said single chain polypeptide comprises domains positioned relative to each other in an N-terminal to C-terminal direction as follows: $V_L$-$C_L$-tether-$V_H$-$CH_1$-hinge-$CH_2$—$CH_3$.

The tether may comprise one or more Glycine (G) and Serine (S) residues. In other embodiments, the tether comprises GGS repeats. The tether, for example, is between 15 and 50 amino acids in length. In a particular embodiment, the tether is between 20 and 32 amino acids in length, for example, 20, 21, 22, 23, 24, 25, 26, 27, 28, 29, 30, 31 or 32 amino acids in length. In certain embodiments, the tether is cleavable. In other embodiments, the tether may or may not be cleavable from the protein. In certain preferred embodiments, the tether is cleavable in two sites at or near the N and C terminus of the tether by the same enzyme. In one embodiment, the tether comprises the cleavage site for proteases such as furin. In a further embodiment, the tether is cleaved by furin at the cleavage site RXRXRR (SEQ ID NO:1), wherein X is any amino acid. In some embodiments, the first hinge-containing polypeptide is a half-antibody and second hinge-containing polypeptide is single chain half-antibody.

In another embodiment, the invention provides a protein comprising a tether and an Fc component complex, wherein the tether may or may not be cleavable from the protein.

In further embodiments, the first and second hinge-containing polypeptides comprise a heteromultimerization domain. The heteromultimerization domain may be a knob into hole mutation, leucine zippers, electrostatic, and the like. The first hinge-containing polypeptide may comprise a knob and the second hinge-containing polypeptide may comprise a hole. In certain embodiments, the hinge-containing polypeptide comprises a half-antibody, and the first half-antibody comprises a knob and the second half-antibody comprises a hole.

In some embodiments, the methods comprises adding Arginine to a final concentration of between 20 mM to 1M prior to adjusting the pH. In some embodiments the Arginine is added to a final concentration of between 50 mM-600 mM. In some embodiments the Arginine is added to a final concentration of between 50 mM-100 mM.

In certain embodiments, the method includes incubating each hinge-containing polypeptide Protein A pool at a pH of between 5 and 8 prior to mixing the first and second half-antibodies. In other embodiments the Protein A pools are mixed and then the pH adjusted to between 5 and 8.

In some embodiments, the methods described herein comprise incubating the mixed half-antibody or mixed hinge-containing polypeptide pool at a temperature of between 15° C. and 39° C., preferably between 18° C.-37° C., more preferably between 20° C.-25° C., more preferably between 32° C.-37° C., for at least 30 minutes.

The hinge-containing polypeptides can be produced by for example, a bacterial cell, a yeast cell, a baculovirus in an insect cell, or a mammalian cell. In certain embodiments, the hinge-containing polypeptide is produced by a bacteria cell, particularly E. coli. In certain other particular embodiments, the hinge-containing polypeptide is produced by a mammalian cell, particularly a CHO cell. In certain particular embodiments, the hinge-containing polypeptide comprises a half-antibody.

The hinge-containing polypeptides can interact to form a dimer or multimer via the heterodimerization domain. In certain embodiments, the interaction between the first and second hinge-containing polypeptides at the interface of the heterodimerization domains is a protuberance-into-cavity interaction, a hydrophobic interaction and/or an electrostatic interaction. In certain other embodiments, the heteromultimerization domain comprises a knob (e.g., protuberance), a hole (e.g., cavity), a leucine zipper, a coiled coil, or a polar amino acid residue capable of forming an electrostatic interaction, or combinations thereof. In certain embodiments, the first hinge-containing polypeptide comprises a knob, and the second hinge-containing polypeptide comprises a hole. In certain other embodiments, the interaction involves both a hydrophobic interaction and an electrostatic interaction. In certain exemplary embodiments, the heteromultimerization domain of each of the first and second hinge-containing polypeptides comprises either a knob or a hole and an amino acid residue capable of forming an electrostatic interaction. It is understood by one skilled in the art that the heterodimerization domain can comprise more than one way of interaction, for example, knob and hole (K&H) and hydrophobic interaction, K&H and leucine zipper, etc. In certain embodiments, the hinge-containing polypeptide further comprises a tether. In certain particular embodiments, the hinge-containing polypeptide comprises a half-antibody.

In certain particular embodiments, the assembly mixture is present in a reducing condition, preferably a weak reducing condition, having an oxidation potential of between −50 to −600 mV, −100 to −600 mV, −200 to −600 mV, −100 to −500 mV, −150 to −300 mV, more preferably between −300 to −500 mV, most preferably about −400 mV, uncer conditions that promote the assembly of the heteromultimeric proteins such as when the pH is between 7 and 9, and the temperature is between 15° C. and 39° C. In certain embodiments, a reductant is added to step c or step d to prepare a desired reducing condition during assembly. In certain other embodiments, the reductant is selected from the group consisting of dithiothreitol (DTT), tris(2-carboxyethyl)phosphine (TCEP), thioglycolic acid, ascorbic acid, thiol acetic acid, glutathione (GSH), Beta-MercaptoEthylAmine, cysteine/cystine, glutathione (GSH), cysteamine/cystamine, glycylcysteine, and beta-mercaptoethanol, preferably GSH. In certain preferred embodiments, the reductant, preferably a weak reductant, is selected from the group consisting of glutathione (GSH), Beta-MercaptoEthylAmine, cysteine/ cystine, glutathione (GSH)/glutathione disulfide (GSSG), cysteamine/cystamine, glycylcysteine, and beta-mercaptoethanol, and preferably GSH. In certain embodiments, the reductant is not DTT.

In certain other embodiments, the reductant is added to the assembly mixture in 2-600×, 2-200×, 2-300×, 2-400×, 2-500×, 2-20×, 2-8×, 20-50×, 50-600×, 50-200×, or 100-300× molar excess, preferably 50-400×, more preferably 100-300×, and most preferably 200×, molar excess with respect to the total amount of the hinge-containing polypeptides. In certain embodiments, the assembly mixture has a pH of between 7 and 9, preferably pH 8.5. In certain embodiments, the hinge-containing polypeptide is a half-antibody.

In some embodiments, the reductant is added to the first and second hinge-containing polypeptides prior to mixing. Preferably the addition is less than 1 hour, more preferably less than 15 minutes, most preferably less than 5 minutes, before mixing.

In certain embodiments, the method further comprises adding a stabilizer to the reaction in one or more of the steps, including without limitation the intermediate pH hold step and the assembly step in the presence or absence of heating. For example, a stabilizer can be added to the hinge-containing polypeptide to prevent or reduce aggregation. In other examples, a stabilizer can be added to the assembly mixture to prevent or reduce aggregation during the assembly of a heteromultimeric protein. In certain particular embodiments, the hinge-containing polypeptide comprises a half-antibody.

In certain particular embodiments, the stabilizer is selected from the group consisting of arginine, histidine and Polyvinylpyrrolidone (PVP). In certain embodiments, the arginine or histidine is an arginine salt or histidine salt. In certain other embodiments, the arginine or histidine is an arginine derivative or histidine derivative. In certain other embodiments, the arginine or histidine is arginine HCl or histidine HCl. In certain embodiments, the arginine is not arginine phosphate.

In certain other embodiments, the method further comprises the step of incubating the assembly mixture in the presence of PVP. In related embodiments, the PVP is added up to 40% (w/v). In certain other embodiments, the PVP is present in the assembly mixture is at a concentration of 2%-6% (w/v), 10%-20%, 2%-10%, 1%, 1.3%, 1.7%, 2%, 2.3%, 2.7%, 3%, 3.3%, 3.7% or 4%, preferably 0.1%-10%, more preferably 2%-6%, and most preferably 4%. In certain embodiments, the PVP is no more than 100 KD, no more than 30 KD, and preferably 10 KD. In certain other embodiments, the PVP is present in less than 10% (w/v), or less than 5% (w/v).

In some embodiments, the stabilizer is arginine present at a concentration of between 20 mM to 1M, 20 mM to less than 1M, 20 mM to 100 mM, 20 mM to 200 mM, 20 mM to 300 mM, 20 mM to 400 mM, 20 mM to 50 mM, 50 mM to 100 mM, 50 nM to 150 mM, 50 mM to 200 mM, 50 mM to 250 mM, or 50 mM to 300 mM. In other embodiments, the stabilizer is histidine present at a concentration of between 20 mM to 1M, 20 mM to less than 1M, 20 mM to 100 mM, 20 mM to 200 mM, 20 mM to 300 mM, 20 mM to 400 mM, 20 mM to 50 mM, 50 mM to 100 mM, 50 nM to 150 mM, 50 mM to 200 mM, 50 mM to 250 mM, or 50 mM to 300 mM. In certain preferred embodiments, the arginine or histidine is added at a concentration of 50 mM or 200 mM. In certain other embodiments, the arginine and/or histidine is added at a concentration of 20 mM to 200 mM, 20 mM to 100 mM, 50 mM to 200 mM or 50 mM to 100 mM. In certain other embodiments, the hinge-containing polypeptide comprises a half-antibody.

In yet another aspect, the invention provides a host cell expressing a hinge-containing polypeptide. In certain embodiments, the hinge-containing polypeptide comprises a half-antibody.

In a further aspect, the invention provides a method of producing a bispecific antibody, comprising the steps of (a) culturing a first host cell engineered to express a first half-antibody specific for a first antigen or a first epitope of an antigen; (b) culturing a second host cell engineered to express a second half-antibody specific for a second antigen or a second epitope of the same antigen; (c) obtaining the first half-antibody from the culture of step a at pH between 4-9, preferably 5-9, in the presence of a first solubilizer; (d) obtaining the second half-antibody from the culture of step b at pH between 4-9, preferably 5-9, in the presence of a second solubilizer; (e) mixing the first and second half-antibodies in a reducing condition to form an assembly mixture; and (f) incubating the assembly mixture to form a bispecific antibody comprising the first and second half-antibodies.

In some embodiments, the first host cell and the second host cell are cultured in separate cultures, and the first half-antibody and the second half-antibody are separately purified from the cultures of the first and second host cells before mixing. In certain embodiments, the first and second host cells are cultured in separate cultures, the cultures are combined, the cells pelleted, optionally homogenized and/or lysed, and the first and second half-antibodies are co-purified by any suitable methods. In certain embodiments, the first and second half-antibodies are co-purified by protein A purification. In further embodiments, the first and second host cells are co-cultured in a mixed culture and the first and second half-antibodies are co-purified.

The host cell can be, for example, a bacterial cell, a yeast cell, a plant cell, an insect cell or a mammalian cell. In certain particular embodiments, the hinge-containing polypeptide or half-antibody is produced by a mammalian cell, such as a CHO cell. In certain other embodiments, the host cell is a bacteria cell, in particular *E. coli*.

In certain additional embodiments, the inventive methods further comprise the step of recovering the heteromultimeric protein or bispecific antibody formed in step (d). The assembled heteromultimeric protein can be further purified by methods described throughout the application or suitable methods known in the art.

In a further aspect, the invention provides compositions comprising a hinge-containing polypeptide and a solubilizer, wherein the pH of the composition is between pH 4-pH 9, preferably between pH 5-9. In certain embodiments, the pH of the composition is at least pH 5, at least pH 5.5, at least pH 5.7, greater than pH 5, greater than pH 5.5, greater than pH 5.7, between 5 and 9, 5 and 8, 5.5 and 8, 5.5 and 9, 5.7 and 8, 5.7 and 9, 6 and 8, 6 and 9, 7 and 8, 7.5 and 8.5, or 7 and 8.5. In certain embodiments, the solubilizer is selected from the group consisting of arginine, histidine and sucrose, preferably arginine and/or histidine. In certain other embodiments, the arginine is an arginine salt and/or histidine is a histidine salt. In certain other embodiments, the arginine is an arginine derivative and/or histidine is a histidine derivative. In certain other embodiments, the arginine or histidine is L-arginine or L-histidine. In certain other embodiments, the arginine or histidine is arginine HCl or histidine HCl.

In certain particular embodiments, the solubilizer is arginine or histidine. In certain other embodiments, the arginine or histidine is present at a concentration of 20 mM, 50 mM, 200 mM, 400 mM, between 20 mM to 1M, between 20 mM to less than 1 M, 20 mM and 200 mM, 20 mM to 400 mM, 20 mM to 100 mM, 50 mM to 100 mM, 50 mM to 200 mM, 50 mM to 300 mM or 50 mM to 400 mM. In certain particular embodiments, the composition comprising both arginine and histidine each present at a concentration of 20 mM, 50 mM, 200 mM, 400 mM, between 20 mM to 1M, between 20 mM to less than 1 M, 20 mM and 200 mM, 20 mM to 400 mM, 20 mM to 100 mM, 50 mM to 100 mM, 50 mM to 200 mM, 50 mM to 300 mM or 50 mM to 400 mM. In certain other embodiments, the composition does not comprise guanidine HCl or urea. In certain embodiments, the composition alternatively or additionally comprises a stabilizer.

In certain particular embodiments, the hinge-containing polypeptide comprises a half-antibody. In certain other particular embodiments, the composition comprises only one type of hinge-containing polypeptide or half-antibody. In certain embodiments, the composition comprises only one type of half-antibody that is a knob half-antibody. In certain other embodiments, the composition comprises only one type of half-antibody that is a hole half-antibody.

In certain particular embodiments, the composition further comprises a second hinge-containing polypeptide, wherein the first hinge-containing polypeptide comprises a knob and the second hinge-containing polypeptide comprises a hole. In certain embodiments, the hinge-containing polypeptide comprises a half-antibody. In certain particular embodiments, the hinge-containing polypeptide is a half-antibody. In certain other embodiments, the half-antibody is of the IgG1, IgG2 or IgG4 isotype.

All embodiments disclosed herein can be combined unless the context clearly dictates otherwise. In addition, any and every embodiment described above applies to any and every aspect of the invention, unless the context clearly indicates otherwise.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 2A shows that elevated pH induced hole half-antibody conformation shift resulting in larger hydrodynamic radius. Such a conformation shift enhanced heterodimerization during assembly. FIG. 2B shows that elevated pH promoted formation of non-covalent knob half-antibody homodimer. Such a conformation shift favored bispecific formation during assembly. Reference is made to Example 2.

FIG. 5B also illustrates that optimization of pH hold of the half antibody pools to drive conformation shifts prior to assembly improved the rate and efficiency of assembly. Reference is made to Example 4.

DETAILED DESCRIPTION

Figure 1B:
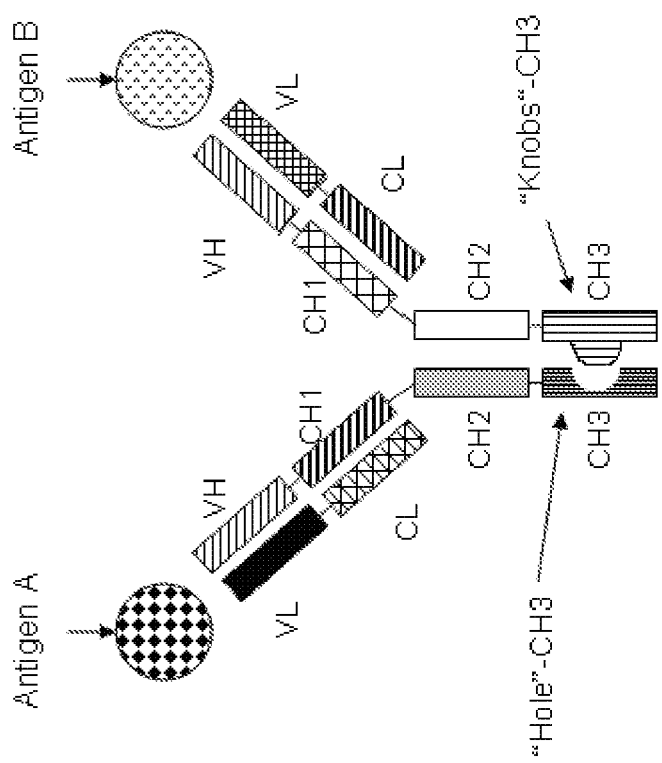
FIG. 1B illustrates a full-length bispecific antibody with a heteromultimerization domain. Not depicted are the inter-heavy chain disulfide bonds in the hinge region. The heteromultimerization domain shown is the knob into hole format.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxyl orientation, respectively.

As used herein, the singular forms "a", "an" and "the" include plural referents unless the context clearly dictates otherwise. For example, reference to "a host cell" means one or more host cells.

The headings provided herein are not limitations of the various aspects or embodiments of the invention which can be had by reference to the specification as a whole. Accordingly, the terms defined immediately below are more fully defined by reference to the specification as a whole.

All embodiments disclosed herein can be combined unless the context clearly dictates otherwise. In addition, any and every embodiment described below applies to any and every aspect of the invention, unless the context clearly indicates otherwise.

I. Definitions

The instant invention provides methods of producing a heteromultimeric protein comprising a first hinge-containing polypeptide and a second hinge-containing polypeptide. The term "hinge-containing polypeptide" as used herein refers to a polypeptide that contains at least one hinge region. In certain embodiments, the hinge region connects multiple domains, for example, a binding domain and an effector domain, and provides some structurally flexibility to the polypeptide for dimerization or multimerization. As an example, the binding domain can be an antigen binding domain of an antibody or a ligand binding domain of a receptor, and the effector domain can be an Fc component of an antibody. In certain embodiments, the first hinge-containing polypeptide is different from the second hinge-containing polypeptide, and the resulting dimer or multimer is a heterodimer or heteromultimer. In certain particular embodiments, the first hinge-containing polypeptide and the second hinge-containing polypeptide bind to two different epitopes on the same target protein. In certain other embodiments, the first hinge-containing polypeptide has a different target binding specificity from that of the second hinge-containing polypeptide and the resulting heterodimer or heteromultimer binds to two or more different target proteins. In certain embodiments, the hinge-containing polypeptide comprises either a naturally occurring or engineered heterodimerization domain. In certain particular embodiments, the hinge-containing polypeptide comprises one or more cysteine residues in the hinge region capable of forming one or more di-sulfide bonds with another hinge-containing polypeptide.

A hinge-containing polypeptide includes without limitation a half-antibody, an immunoadhesin, and functional fragment thereof. The term "functional fragment" as used herein refers to a fragment, i.e., less than the full-length, of the hinge-containing polypeptide, which still retains the desired function, for example, retaining the target or antigen-binding activity, the Fc effector activity and/or dimerization/multimerization ability. In certain particular embodiments, the first hinge-containing polypeptide and second hinge-containing polypeptide each is a half-antibody with different antigen binding specificity, and the resulting dimer or multimer is a bispecific or multispecific antibody. In certain embodiments, the resulting heteromultimeric protein comprises a half-antibody and an immunoadhesin.

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

A naturally occurring basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for p and c isotypes. Each L chain has, at the N-terminus, a variable domain ($V_L$) followed by a constant domain ($C_L$) at the C-terminus. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFRI), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In one embodiment, for the VL, the subgroup is subgroup kappa I as in Kabat. In one embodiment, for the VH, the subgroup is subgroup III as in Kabat.

One example of an "intact" antibody is one that comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof.

"Antibody fragments" comprise a portion of an intact antibody, preferably the antigen binding or a variable region of the intact antibody. Examples of antibody fragments include Fab, Fab', F(ab')$_2$, and Fv fragments; diabodies (Db); tandem diabodies (taDb), linear antibodies (e.g., U.S. Pat. No. 5,641,870, Example 2; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-CH3 and (scFV)4-Fc).

Figure 1A:
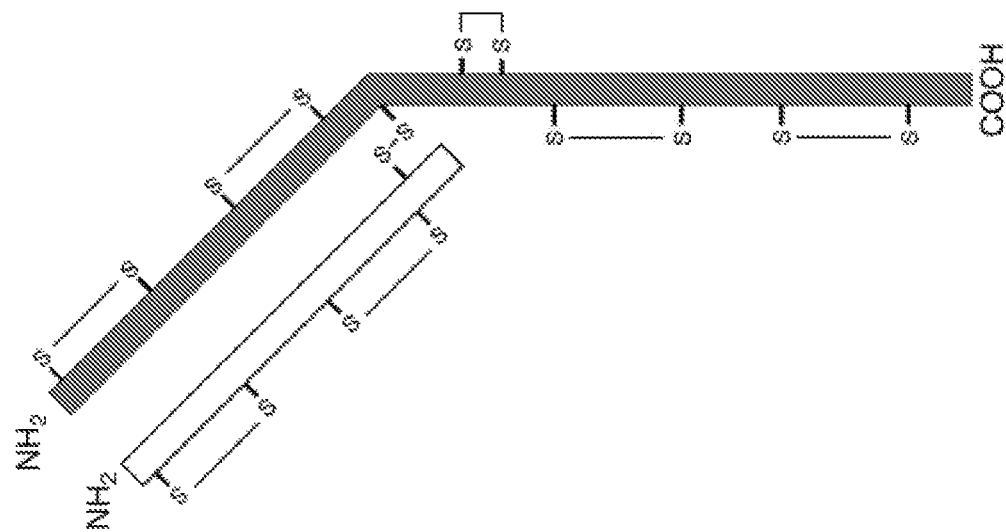
FIG. 1A illustrates a fully oxidized half-antibody. Not shown is the "knob" or "hole" or other heterodimerization domains. The half-antibody depicted in this figure is an IgG1 isotype. One skilled in the art will appreciate that the other immunoglobulin isotypes can be envisioned as half-antibodies with the corresponding inter- and intra-chain bonds. In an intact antibody the hinge cysteines will form inter-chain disulfide bonds.
Figure 1C:
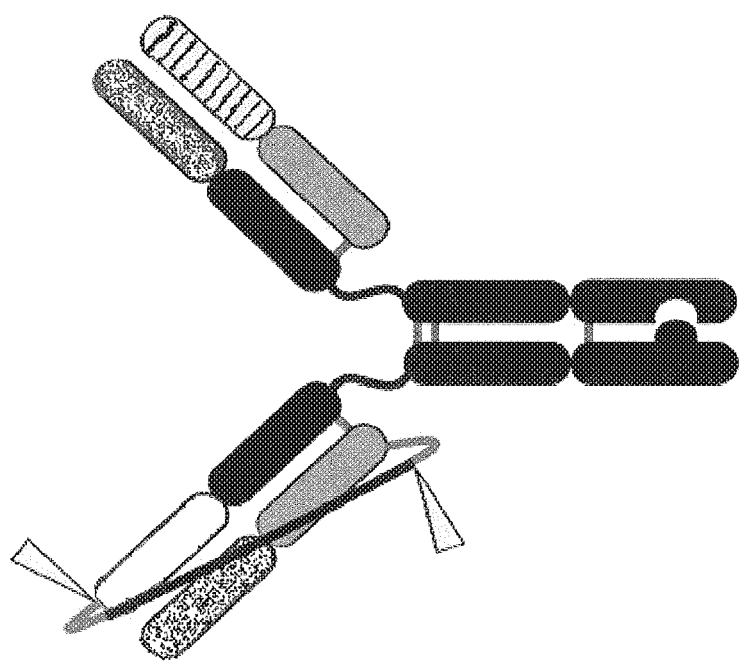
FIG. 1C is a cartoon representation of a bispecific antibody comprising a heteromultimerization domain (knob into hole), a furin cleavable tether and an optional extra disulfide bond (S354). The inter-heavy chain disulfide bonds in the hinge region are also shown. The furin cleavage sites are indicated by the triangles. Although the furin cleavable tether is shown on the half-antibody comprising the knob it can also be utilized on the hole half-antibody or on both the knob and hole half-antibodies.

The term "half-antibody" as used herein refers to one immunoglobulin heavy chain associated with one immunoglobulin light chain. An exemplary half-antibody is depicted in FIG. 1A. One skilled in the art will readily appreciate that a half-antibody may encompass a fragment thereof and may also have an antigen binding domain consisting of a single variable domain, e.g., originating from a camelidae.

The instant inventors unexpectedly discovered that pH optimization or adjustment of half-antibodies eluted from a Protein A column or other matrix at low pH induced conformation shift of hinge-containing polypeptides such as half-antibodies. The pH optimization to an intermediate pH, sometimes referred to as pH hold or intermediate pH hold throughout this disclosure, may cause precipitation or aggregation of the half-antibodies. Thus, in certain embodiments, the method of producing a heteromultimeric protein comprises the step of providing a first or second hinge-containing polypeptide at pH 5-9 in the presence of a first or a second solubilizer, respectively.

A solubilizer as used herein is defined as a reagent that prevents or reduces precipitation of a hinge-containing polypeptide, such as a half-antibody. Suitable solubilizer includes without limitation, arginine and histidine, or a salt or derivative thereof, and sucrose. In certain embodiments, the solubilizer is arginine and/or histidine. In certain embodiments, solubilizer prevents or reduces precipitation induced by intermediate pH hold and/or heating. In certain particular embodiments, a solubilizer is added before the intermediate pH hold (i.e., before adjusting to intermediate pH), and/or heating. In certain embodiments, the arginine or histidine is an arginine salt or histidine salt. In certain other embodiments, the arginine or histidine is an arginine derivative or histidine derivative. Reduction of precipitation can lead to increased yield of the desired assembled final product.

Imidazole and guanidine have been used to solubilize protein for general protein preparation and purification. However, it was unexpectedly discovered that imidazole and guanidine alone, without being in the context of histidine or arginine, respectively, were insufficient to improve the overall yield of assembled heteromulimeric protein as described herein, such as bispecific antibody. In certain embodiments, imidazole and guanosine can denature the proteins.

Similarly, detergents such as guanidine HCl and urea are commonly used to reduce aggregation/precipitation in general but they can completely denature the protein. Thus, in certain embodiments, the solubilizer prevents or reduces precipitation without denaturing the protein of interest. Thus, in certain particular embodiments, the solubilizer is not guanidine HCl, guanidine, imidazole or urea. And in certain other embodiments, the compositions of the invention do not comprise guanidine HCl or urea. In certain other embodiments, the solubilzer is not Tween or PEG.

In addition, a stabilizer can be added, for example, during an intermediate pH hold of each half-antibody or during assembly at or right after mixing the hinge-containing polypeptides or half-antibodies. A stabilizer can be added to the reaction of one or more or all of the steps of the inventive methods to prevent or reduce aggregation of the hinge-containing polypeptides or half-antibodies, before, during and/or after assembly.

Aggregates can be detected as high molecular weight species and, in the context of half-antibodies, high molecular weight species with a molecular weight larger than 150 kDa. Aggregates can be detected and quantified by, for example, size exclusion chromatography or other suitable methods. In certain other embodiments, the aggregates detected by the size exclusion chromatography can pass through a 0.2 urn sterile filter. Precipitated proteins, on the other hand, can be composed of denatured proteins or aggregated proteins which can form very large complex. Several reagents have been tested and were determined ineffective or not suitable for use as stabilizers, for example, imidazole, 3-(N-morpholino)propanesulfonic acid (MOPS), 2-(N-morpholino) ethanesulfonic acid (MES), cyclodextrin, $CuSO_4$ and NaOAc. Thus, in certain embodiments, the stabilizer does not include inorganic salts or transition metals. Suitable stabilizer includes without limitation PVP, histidine and arginine. Reduction of aggregation can lead to increased yield of the desired assembled final product.

PVP is a water soluble uncharged polymer with a pyrrolidone group. In certain embodiments, other uncharged polar polymers, other reagents or compounds, especially compounds with similar structure and properties with the suitable stabilizers described herein may be suitable stabilizers for use in the invention. It is within the ability of one skilled in the art to determine a suitable stabilizer by analyzing the effect of the compound on the levels of aggregation by methods known in the art, including the methods provided herein.

A reagent may be characterized as both a solubilizer and a stabilizer. For example, arginine can be used as a solubilizer to reduce precipitation of half-antibodies during intermediate pH hold and/or heating, as well as a stabilizer to reduce aggregation during the assembly step. Similarly, histidine can be used as a solubilizer to reduce precipitation as well as a stabilizer to reduce aggregation of half-antibodies, during the intermediate pH hold and/or heating. Without being limited to any particular mechanisms, in certain embodiments, both a solubilizer and a stabilizer can work by preventing interaction of hydrophobic patches on the surfaces of proteins that can lead to aggregation. In other embodiments, both a solubilizer and a stabilizer can function by forming clathrates to prevent undesirable interaction of proteins.

The term "single chain half-antibody" as used herein refers to a single chain polypeptide comprising a VL domain, optionally a CL domain, a tether, a VH domain, optionally a CH1 domain, a hinge domain, a CH2 domain and a CH3 domain, wherein said domains are positioned relative to each other in an N-terminal to C-terminal direction as follows: VL-tether-VH-hinge-CH2-CH3 or VL-CL-tether-VH-CH1-hinge-CH2-CH3.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The expression "linear antibodies" generally refers to the antibodies described in Zapata et al., Protein Eng. 8(10): 1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies and other Fc fusions).

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxyl terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The term "one-armed antibody" or "one-armed antibodies" refers to an antibody that comprises (1) a variable domain joined by a peptide bond to a polypeptide comprising a CH2 domain, a CH3 domain or a CH2-CH3 domain and (2) a second CH2, CH3 or CH2-CH3 domain, wherein a variable domain is not joined by a peptide bond to a polypeptide comprising the second CH2, CH3 or CH2-CH3 domain. In one embodiment, the one-armed antibody comprises 3 polypeptides (1) a first polypeptide comprising a variable domain (e.g., VH), CH1, CH2 and CH3, (2) a second polypeptide comprising a variable domain (e.g., VL) and a CL domain, and (3) a third polypeptide comprising a CH2 and CH3 domain. In an embodiment, the third polypeptide does not comprise a variable domain. In another embodiment, the one-armed antibody has a partial hinge region containing the two cysteine residues which form disulfide bonds linking the constant heavy chains. In one embodiment, the variable domains of the one armed antibody form an antigen binding region. In another embodiment, a variable domain of the one armed antibody is a single variable domain, wherein each single variable domain is an antigen binding region.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Complex" or "complexed" as used here in refers to the association of two or more molecules that interact with each other through bonds and/or forces (e.g., van der Waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

The term "heteromultimer" or "heteromultimeric" as used herein describes two or more polypeptides that interact with each other by a non-peptidic, covalent bond (e.g., disulfide bond) and/or a non-covalent interaction (e.g., hydrogen bonds, ionic bonds, Van der Waals forces, and hydrophobic interactions), wherein at least two of the molecules have different sequences from each other.

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjærgaard et al.—Novo Nordisk: describing ionic interactions); WO 2009089004 (Kannan et al.—Amgen: describing electrostatic steering effects); WO 2010/034605 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein. In certain embodiments, the hinge-containing polypeptide comprises one or more heterodimerization domains.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

An antibody of this invention "which binds" an antigen of interest is one that binds the antigen with sufficient affinity such that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of an antibody to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In one embodiment, the term "specific binding" refers to binding where a molecule binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value" according to this invention is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 pg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 pg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a polypeptide of this invention, such as an antibody, fragment, or derivative thereof, means having the ability to bind to a biological molecule, except where specified otherwise.

"Peptibody" or "peptibodies" refers to a fusion of randomly generated peptides with an Fc domain. See U.S. Pat. No. 6,660,843, issued Dec. 9, 2003 to Feige et al. (incorporated by reference in its entirety). They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety.

"Affibodies" or "Affibody" refers to the use of a protein liked by peptide bond to an Fc region, wherein the protein is used as a scaffold to provide a binding surface for a target molecule. The protein is often a naturally occurring protein such as staphylococcal protein A or IgG-binding B domain, or the Z protein derived therefrom (see Nilsson et al (1987), Prot Eng 1, 107-133, and U.S. Pat. No. 5,143,844) or a fragment or derivative thereof. For example, affibodies can be created from Z proteins variants having altered binding affinity to target molecule(s), wherein a segment of the Z protein has been mutated by random mutagenesis to create a library of variants capable of binding a target molecule. Examples of affibodies include U.S. Pat. No. 6,534,628. Nord K et al, Prot Eng 8:601-608 (1995) and Nord K et al, Nat Biotech 15:772-777 (1997). Biotechnol Appl Biochem. 2008 June; 50(Pt 2):97-112.

"Isolated" heteromultimer or complex means a heteromultimer or complex which has been separated and/or recovered from a component of its natural cell culture environment. Contaminant components of its natural environment are materials which would interfere with diagnostic or therapeutic uses for the heteromultimer, and may include enzymes, hormones, and other proteinaceous or nonproteinaceous solutes. In preferred embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

By "linked" or "links" as used herein is meant either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "tether" as used herein is meant an amino acid linker that joins two other amino acid sequences. A tether as described herein can link the N-terminus of an immunoglobulin heavy chain variable domain with the C-terminus of an immunoglobulin light chain constant domain. In particular embodiments, a tether is between about 15 and 50 amino acids in length, for example, between 20 and 26 amino acids in length (e.g., 20, 21, 22, 23, 24, 25, or 26 amino acids in length). A tether may be "cleavable," for example, by auto-cleavage, or enzymatic or chemical cleavage using methods and reagents standard in the art. In certain particular embodiments, the tether comprises Gly-Gly-Ser repeats.

Enzymatic cleavage of a "linker" or a "tether" may involve the use of an endopeptidase such as, for example, Lys-C, Asp-N, Arg-C, V8, Glu-C, chymotrypsin, trypsin, pepsin, papain, thrombin, Genenase, Factor Xa, TEV (tobacco etch virus cysteine protease), Enterokinase, HRV C3 (human rhinovirus C3 protease), Kininogenase, as well as subtilisin-like proprotein convertases (e.g., Furin (PC1), PC2, or PC3) or N-arginine dibasic convertase. Chemical cleavage may involve use of, for example, hydroxylamine, N-chlorosuccinimide, N-bromosuccinimide, or cyanogen bromide.

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue. In certain embodiments, the half-antibody further comprises a K222A mutation in the hinge region to remove the endogenous Lys-C endopeptidase cleavage site to preserve the structure of the half-antibody or the assembled bispecific antibody upon cleavage of the tether by Lys-C endopeptidase.

"Hinge region" is generally defined as stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present invention, FcγR binding was generally attributed to amino acid residues in the lower hinge region of an IgG Fc region.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22:161-206 (1985).

The "CH3 domain" comprises the stretch of residues C-terminal to a CH2 domain in an Fc region (i.e. from about amino acid residue 341 to about amino acid residue 447 of an IgG).

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc complex" as used herein refers to two CH2 domains of an Fc region interacting together and/or two CH3 domains of an Fc region interacting together, wherein the CH2 domains and/or the CH3 domains interact through bonds and/or forces (e.g., van der Weals, hydrophobic, hydrophilic forces) that are not peptide bonds.

"Fc component" as used herein refers to a hinge region, a CH2 domain or a CH3 domain of an Fc region.

"Fc CH component" or "FcCH" as used here in refers to a polypeptide comprising a CH2 domain, a CH3 domain, or CH2 and CH3 domains of an Fc region.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis: down regulation of cell surface receptors (e.g., B cell receptor); and B cell activation.

In the present invention, "a reducing condition" is defined based on the redox potential in a reaction (for example in an assembly mixture) to mean that the redox potential of the reaction is negative (−). The redox potential of the reaction under reducing conditions is preferably between about −50 to −600 mV, −100 to −600 mV, −200 to −600 mV, −100 to −500 mV, −150 to −300 mV, more preferably between about −300 to −500 mV, most preferably about −400 mV.

Any suitable methods can be used to prepare a desired reducing condition. For example, a desired reducing condition can be prepared by adding a reductant/reducing agent to the reaction (such as an assembly mixture of the invention). Suitable reductants include without limitation dithiothreitol (DTT), tris(2-carboxyethyl)phosphine (TCEP), thioglycolic acid, ascorbic acid, thiol acetic acid, glutathione (GSH), Beta-MercaptoEthylAmine, cysteine/cystine, GSH/glutathione disulfide (GSSG), cysteamine/cystamine, glycylcysteine, and beta-mercaptoethanol, preferably GSH. In certain particular embodiments, the reductant is a weak reductant including without limitation GSH, Beta-MercaptoEthylAmine, cysteine/cystine, GSH/GSSG, cysteamine/cystamine, glycylcysteine, and beta-mercaptoethanol, preferably GSH. In certain preferred embodiments, the reductant is GSH. It is within the ability of one of ordinary skill in the art to select suitable reductants at suitable concentrations and under suitable experimental conditions to achieve in a reaction the desired reducing condition. For example, 10 mM L-reduced glutathione in a solution with a bispecific antibody protein concentration of 10 g/L at 20° C. will result in a starting redox potential of about −400 mV. One of skill in the art can use any suitable methods to measure the redox potential in a given reaction.

The reducing condition of the reaction can be estimated and measured using any suitable methods known in the art. For example, the reducing condition can be measured using a resazurin indicator (discolorization from blue to colorless in reducing conditions). For more precise measurement, a redox-potential meter (such as an ORP Electrode made by BROADLEY JAMES®) can be used.

Alternatively, a reducing condition can be prepared by removing dissolved gases, especially dissolved oxygen, under reduced pressure of about 10 mmHg or less, preferably about 5 mmHg or less, more preferably about 3 mmHg or less, for about 1 to 60 minutes, preferably for about 5 to 40 minutes.

In the present invention, it is preferred that reducing conditions are maintained from immediately after mixing the first and second hinge-containing polypeptides (such as half-antibodies) throughout the assembly step. In certain embodiments, the reaction or the assembly mixture is maintained in reducing conditions preferably for about 50% or more, more preferably for about 70% or more, further more preferably for about 90% or more of the reaction time. It is particularly preferred that the redox-potential of the reaction medium is maintained from about −200 to −600 mV, more preferably between −300 to −500 mV, most preferably about −400 mV, for about 50% or more, more preferably for about 70% or more, further more preferably for about 90% or more of the reaction time.

In certain particular embodiments, the reducing condition is a weak reducing condition. The term "weak reductant" or "weak reducing condition" as used herein refers to a reducing agent or a reducing condition prepared by the reducing agent having a negative oxidation potential at 25° C. The oxidation potential of the reductant is preferably between −50 to −600 mV, −100 to −600 mV, −200 to −600 mV, −100 to −500 my, −150 to −300 mV, more preferably between about −300 to −500 mV, most preferably about −400 mV, when the pH is between 7 and 9, and the temperature is between 15° C. and 39° C. One skilled in the art will be able to select suitable reductants for preparing a desired reducing condition. The skilled researcher will recognize that a strong reductant, i.e., one that has a more negative oxidation potential than above mentioned reductants for the same concentration, pH and temperature, may be used at a lower concentration. In a preferred embodiment, the proteins will be able to form disulfide bonds in the presence of the reductant when incubated under the above-recited conditions. Examples of a weak reductant include without limitation glutathione, Beta-MercaptoEthylAmine, cystine/cysteine, GSH/GSSG, cysteamine/cystamine, glycylcysteine, and beta-mercaptoethanol. In certain embodiments, an oxidation potential similar to that of 200× molar ratio of GSH:Antibody can be used as a point of reference for a weakly reducing condition at which efficient assembly using other reductants can be expected.

An "assembly mixture" is a solution comprising a first hinge-containing polypeptide, a second hinge-containing polypeptide. In certain embodiments, the assembly mixture is present in a reducing condition. In some embodiments, the assembly mixture is present in a weak reducing condition. In certain other embodiments, the assembly mixture further comprises a weak reductant. The oxidation potential of the assembly mixture is between −50 to −600 mV, −100 to −600 mV, −200 to −600 mV, −100 to −500 mV, −150 to −300 mV, more preferably between about −300 to −500 mV, most preferably about −400 mV, when the pH is between 7 and 9, and the temperature is between 15° C. and 39° C.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, N Y, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

II. Construction of Heteromultimeric Proteins

Typically, the heteromultimeric proteins described herein will comprise a significant portion of an antibody Fc region. In other aspects, however, the heavy chain comprises only a portion of the CA $C_H2$, and/or $C_H3$ domains.

Heteromultimerization Domains

The heteromultimeric proteins comprise a heteromultimerization domain. To generate a substantially homogeneous population of heterodimeric molecule, the heterodimerization domain must have a strong preference for forming heterodimers over homodimers. Although the heteromultimeric proteins exemplified herein use the knobs into holes technology to facilitate heteromultimerization those skilled in the art will appreciate other heteromultimerization domains useful in the instant invention.

Knobs into Holes

The use of knobs into holes as a method of producing multispecific antibodies is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S. See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE 1

Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from *Handbook of Chemistry and Physics*, 43rd ed. Cleveland, Chemical Rubber Publishing Co., 1961.
[b]Values from A. A. Zamyatnin, *Prog. Biophys. Mol. Biol.* 24: 107-123, 1972.
[c]Values from C. Chothia, *J. Mol. Biol.* 105: 1-14, 1975. The accessible surface area is defined in FIGS. 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine. Exemplary amino acid substitutions in the CH3 domain for forming the protuberance include without limitation the T366W substitution.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 1 above. The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan. Exemplary amino acid substitutions in the CH3 domain for generating the cavity include without limitation the T366S, L368A, Y407A, Y407T and Y407V substitutions. In certain embodiments, the knob half-antibody comprises T1366W substitution, and the hole half-antibody comprises the T366S/L368A/Y407V substitutions.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 1 above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original or template nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*, M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotamers" (e.g. about 3-6). A "rotamer" is an energetically favorable conformation of an amino acid side chain. The number of rotamers of the various amino acid residues are reviewed in Ponders and Richards, J. Mol. Biol. 193: 775-791 (1987).

III. Vectors, Host Cells and Recombinant Methods

For recombinant production of a heteromultimeric protein (e.g., a bispecific antibody) of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. It will be appreciated that constant regions of any isotype can be used for this purpose, including IgG, IgM, IgA, IgD, and IgE constant regions, and that such constant regions can be obtained from any human or animal species. In certain embodiments, the constant region is from IgG, particularly IgG1, IgG2 or IgG4.

A host cell is engineered such that it expresses a hinge-containing polypeptide comprising a heterodimerization domain wherein the host cell does not express a hinge-containing polypeptide comprising a second heterodimerization domain.

a. Generating Heteromultimeric Proteins Using Prokaryotic Host Cells i. Vector Construction

Polynucleotide sequences encoding polypeptide components of the heteromultimeric proteins (e.g., an antibody) of the invention can be obtained using standard recombinant techniques. Desired polynucleotide sequences may be isolated and sequenced from, for example, antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding, for example, the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of the expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to operably ligate them to cistrons encoding the genes of the heteromultimeric protein, e.g., the target light and heavy chains (Siebenlist et al., (1980) Cell 20: 269), using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are Sill signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. See Proba and Pluckthun *Gene*, 159:203 (1995).

Prokaryotic host cells suitable for expressing heteromultimeric proteins (e.g., antibodies) of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac lq IacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli,* 1776 (ATCC 31,537) and *E. coli* RV308 (ATCC 31,608) are also suitable. In one embodiment, *E. coli* Δlpp finds particular use. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Polypeptide Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique commonly used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the first and second hinge-containing host cells are cultured separately and the expressed polypeptides of the present invention are secreted into and recovered from the periplasm of the host cells separately. In a second embodiment, the first and second hinge-containing host cells are cultured separately and prior to the isolation of the hinge-containing polypeptides, the two host cell cultures are mixed together and the cells pelleted. In a third embodiment, the first and second hinge-containing host cells are cultured separately, centrifuged and resuspended separately and then mixed together prior to isolation of the hinge-containing polypeptides. In fourth embodiment, the first and second hinge-containing host cells are cultured together in the same culture vessel. Protein recovery typically involves disrupting the microorganism cell membrane, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported or secreted into the culture media and isolated therein. Recombinant proteins expressed with an exogenous sequence tag (or epitope tag) can facilitate the purification step. The technique of cloning and purification of proteins containing an exogenous sequence tag (including without limitation the His tag and GST tag) is well known in the art. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay. The isolated polypeptides will be used to produce the heteromultimeric proteins.

In one aspect of the invention, heteromultimeric protein (e.g., antibody) production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted heteromultimeric proteins (e.g., antibodies), additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605;

Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbial.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), *Proc. Natl. Acad. Sci. USA* 95:2773-2777; Georgiou et al., U.S. Pat. No. 5,264,365; Georgiou et al., U.S. Pat. No. 5,508,192; Hara et al., *Microbial Drug Resistance,* 2:63-72 (1996). In one embodiment, *E. coli* strains deficient for proteolytic enzymes and transformed with plasmids overexpressing one or more chaperone proteins are used as host cells in the expression system of the invention. In a second embodiment, the *E. coli* strain is deficient for a lipoprotein of the outer membrane (Δlpp).

iii. Heteromultimeric Protein Purification

In one embodiment, the heteromultimeric protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on an ion-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of, for example, the half-antibody or full length antibody products of the invention. Protein A is a 41 kD cell wall protein from *Staphylococcus aureus* which binds with a high affinity to the Fc region of antibodies. Lindmark et al. (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants nonspecifically bound to the solid phase. The heteromultimeric protein (e.g., antibody) is recovered from the solid phase by elution.

b. Generating Heteromultimeric Proteins Using Eukaryotic Host Cells

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired heteromultimeric protein(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired hinge-containing polypeptide(s) (e.g., antibody) nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Desired hinge-containing polypeptide(s) (e.g., half-antibody) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding the desired hinge-containing polypeptide(s) (e.g., antibody) by higher eukaryotes can be increased by inserting an enhancer sequence into the vector. Many enhancer sequences are now known from mammalian genes (e.g., globin, elastase, albumin. α-feto-protein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/- DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for desired hinge-containing polypeptide(s) (e.g., antibody) production and cultured in conventional nutrient media modified as appropriate for inducing promoters, selecting transformants, or amplifying the genes encoding the desired sequences.

viii. Culturing the Host Cells

The host cells used to produce a desired hinge-containing polypeptide(s) (e.g., antibody) of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Heteromultimeric Proteins

When using recombinant techniques, the hinge-containing polypeptides can be produced intracellularly, or directly secreted into the medium. If the hinge-containing polypeptide is produced intracellularly, as a first step, the particulate debris, either host cells or lysed fragments, are removed, for example, by centrifugation or ultrafiltration. Where the hinge-containing polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimer composition prepared from the cells can be purified using, for example, ion exchange, hydrophobic interaction chromatography, hydroxylapatite chromatography, gel electrophoresis, dialysis, and affinity chromatography, with affinity chromatography being the preferred purification technique. Combinations of the above-mentioned techniques are also contemplated. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt). The production of the heteromultimeric proteins can alternatively or additionally (to any of the foregoing particular methods) comprise dialyzing a solution comprising a mixture of the polypeptides.

x. Antibody Production Using Baculovirus

Recombinant baculovirus may be generated by co-transfecting a plasmid encoding an antibody or antibody fragment and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antibody sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antibody or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antibody can then be purified, for example, by Ni2+-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM MgCl2; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 µm filter. A Ni2+-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaCl; 10% glycerol pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with Ni2+-NTA-conjugated to alkaline phosphatase (Qiagen). Fractions containing the eluted His10-tagged antibody are pooled and dialyzed against loading buffer.

Alternatively, purification of the antibody can be performed using known chromatography techniques, including for instance, Protein A or protein G column chromatography. In one embodiment, the antibody of interest may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available.

IV. Target Molecules

Examples of molecules that may be targeted by a heteromultimeric protein of this invention include, but are not limited to, soluble serum proteins and their receptors and other membrane bound proteins (e.g., adhesins). See WO2011/133886, which is incorporated by reference herein in its entirety.

In another embodiment the heteromultimeric protein of the invention is capable of binding one, two or more cytokines, cytokine-related proteins, and cytokine receptors selected from the group consisting of BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2). FGF7 (KGF), FGF9, FGF10, FGF1 1, FGF12, FGF12B, FGF14, FGF16, FGF17, FGF19, FGF20, FGF21, FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), IL1A, IL1 B, IL2, IL3, IL4, IL5, IL6, IL7, IL8, IL9, IL10, IL1 1, IL12A, IL12B, IL13, IL14, IL15, IL16, IL17, IL17B, IL18, IL19, IL20, IL22, IL23, 124, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNFSFIO (TRAIL), TNFSF1 I (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1 R2, IL1 RL1, IL1 RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, 11.17R, IL18R1, IL20RA, IL21 R, IL22R, IL1 HY1, IL1 RAP, IL1 RAPL1, IL1 RAPL2, IL1 RN, IL6ST, IL18BP, IL18RAP, IL22RA2, AIFI, HGF, LEP (leptin), PTN, and THPO.

In another embodiment, a target molecule is a chemokine, chemokine receptor, or a chemokine-related protein selected from the group consisting of CCLI (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL2? (CTACK/ILC), CCL28, CXCLI (GROI), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDFI), CXCL13, CXCL14, CXCL16, PF4 (CXCL4), PPBP (CXCL7), CX3CL1 (SCYDI), SCYEI, XCLI (lymphotactin), XCL2 (SCM-Ib), BLRI (MDR15), CCBP2 (D6/JAB61), CCR1 (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRIO), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, and VHL.

In another embodiment the heteromultime c proteins of the invention are capable of binding one or more targets selected from the group consisting of ABCFI; ACVRI; ACVRIB; ACVR2; ACVR2B; ACVRLI; ADORA2A; Aggrecan; AGR2; AICDA; AIFI; AIGI; AKAPI; AKAP2; AMH; AMHR2; ANGPTI; ANGPT2; ANGPTL3; ANGPTL4; ANPEP; APC; APOCI; AR; AZGPI (zinc-a-glycoprotein); B7.1; B7.2; BAD; BAFF (BLys); BAGI; BAH; BCL2; BCL6; BDNF; BLNK; BLRI (MDR15); BMPI; BMP2; BMP3B (GDFIO); BMP4; BMP6; BMP8; BMPRIA; BMPRIB; BMPR2; BPAGI (plectin); BRCAI; C19orf10 (IL27w); C3; C4A; C5; C5R1; CANTI; CASP1; CASP4; CAVI; CCBP2 (D6/JAB61); CCLI (1-309); CCLII (eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL2? (CTACK/ILC); CCL28; CCL3 (MTP-Ia); CCL4 (MOP-Ib); CCL5 (RANTES); CCLI (MCP-3); CCL8 (mcp-2); CCNAI; CCNA2; CCNDI; CCNEI; CCNE2; CCRI (CKRI/HM145); CCR2 (mcp-IRB/RA); CCR3 (CKR3/CMKBR3): CCR4; CCR5 (CMKBR5/ChemR13); CCR6 (CMKBR6/CKR-L3/STRL22/DRY6); CCR7 (CKR7 EBII); CCR8 (CMKBR8/TERI/CKR-L1); CCR9 (GPR-9-6); CCRLI (VSHKI); CCRL2 (L-CCR); CD164; CD19; CDIC; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDHI (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLRI; CMKORI (ROCI); CNRI; COL18A1; COLIAI; COL4A3; COL6A1; CR2; CRP; CSFI (M-CSF); CSF2 (GM-CSF); CSF3 (GCSF); CTLA4; CTNNBI (b-catenin); CTSB (cathepsin B); CX3CL1 (SCYDI); CX3CR1 (V28); CXCLI (GROI); CXCL10 (IP-10); CXCLII (I-TAC/IP-9); CXCL12 (SDFI); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYCI; CYSLTRI; DAB2IP; DES; DKFZp451 J01 18; DNCLI; DPP4; E2F1; ECGFI; EDGI; EFNAI; EFNA3; EFNB2; EGF; EGFR; ELAC2; ENG; EN01; EN02; EN03; EPHB4; EPO; ERBB2 (Her-2); EREG; ERK8; ESRI; ESR2; F3 (TF); FADD; FasL; FASN; FCERIA; FCER2; FCGR3A; FGF; FGFI (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FELI (EPSILON); FILL (ZETA); FLJ12584; FLJ25530; FLRTI (fibronectin); FLTI; FOS; FOSLI (FRA-I); FY (DARC); GABRP (GABAa); GAGEBI; GAGECI; GALNAC4S-6ST; GATA3; GDF5; GFI1; GGT1; GM-CSF; GNASI; GNRHI; GPR2 (CCRIO); GPR31; GPR44; GPR81 (FKSG80); GRC-CIO (CIO); GRP; GSN (Gelsolin); GSTPI; HAVCR2; HDAC4; HDAC5; HDAC7A; HDAC9; HGF; HIFIA; HDPI; histamine and histamine receptors; HLA-A; HLA-DRA; HM74; HMOXI; HUMCYT2A; ICEBERG; ICOSL; ID2; IFN-a; IFNAI; IFNA2; IFNA4; IFNA5; IFNA6; IFNA7; IFNB1; IFNgamma; DFNWI; IGBPI; IGFI; IGFIR; IGF2; IGFBP2; IGFBP3; IGFBP6; IL-I; IL10; IL10RA; IL10RB; IL1 1; IL1 1 RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1 B; IL1F10; IL1 F5; IL1 F6; IL1 F7; IL1 F8; IL1 F9; IL1 HYI; IL1 RI; IL1 R2; IL1 RAP; IL1 RAPL1; IL1 RAPL2; IL1 RL1; IL1 RL2, IL1RN; IL2; IL20; IL20RA: IL21 R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAI; ITGA2; ITGA3; ITGA6 (a6 integrin); ITGAV; ITGB3; ITGB4 (b 4 integrin); JAGI; JAKI; JAK3; JUN; K6HF; KAII; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIBI; midkine; MEF; MIP-2; MK167; (Ki-67); MMP2; MMP9; MS4A1; MSMB; MT3 (metallothionectin-III); MTSSI; MUCI (mucin); MYC; MYD88; NCK2; neurocan; NFKBI; NFKB2; NGFB (NGF); NGFR; NgR-Lingo; NgR-Nogo66 (Nogo); NgR-p75; NgR-Troy; NMEI (NM23A); NOX5; NPPB; NROBI; NROB2; NRIDI; NR1 D2; NR1 H2; NR1 H3; NR1 H4; NR1 12; NR1 13; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRPI; NRP2; NT5E; NTN4; ODZI; OPRDI; P2RX7; PAP; PARTI: PATE; PAWR; PCA3; PCNA; PDGFA; PDGFB; PECAMI; PF4 (CXCL4); PGF; PGR; phosphacan; PIAS2; PIK3CG; PLAU (uPA); PLG; PLXDCI; PPBP (CXCL7); PPID; PRI; PRKCQ; PRKDI; PRL; PROC; PROK2; PSAP; PSCA; PTAFR; PTEN;

PTGS2 (COX-2); PTN; RAC2 (p21 Rac2); RARB; RGSI; RGS13; RGS3; RNFIIO (ZNF144); ROBO2; S100A2; SCGB1 D2 (lipophilin B); SCGB2A1 (mammaglobin2); SCGB2A2 (mamnnaglobin 1); SCYEI (endothelial Monocyte-activating cytokine); SDF2; SERPINAI; SERPINA3; SERP1 NB5 (maspin); SERPINEI (PAI-1); SERPDMF1; SHBG; SLA2; SLC2A2; SLC33A1; SLC43A1; SLIT2; SPPI; SPRRIB (Spri); ST6GAL1; STABI; STATE; STEAP; STEAP2; TB4R2; TBX21; TCPIO; TDGFI; TEK; TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLRIO; TLR2; TLR3; TLR4; TLR5; TLR6; TLR7; TLR8; TLR9; TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSFIO (TRAIL); TNFSFI 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1 BB ligand); TOLLIP; Toll-like receptors; TOP2A (topoisomerase Ea); TP53; TPMI; TPM2; TRADD; TRAFI; TRAF2; TRAF3; TRAF4; TRAF5; TRAF6; TREMI; TREM2; TRPC6; TSLP; TWEAK; VEGF; VEGFB; VEGFC; versican; VHL C5; VLA-4; XCLI (Iymphotactin); XCL2 (SCM-Ib); XCRI (GPR5 CCXCRI); YYI; and ZFPM2.

Preferred molecular target molecules for antibodies encompassed by the present invention include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mad, p150.95, VLA-4, ICAM-1, VCAM, alpha4/beta7 integrin, and alphav/beta3 integrin including either alpha or beta subunits thereof (e.g., anti-CD1 1 a, anti-CD18 or anti-CD1 1 b antibodies); growth factors such as VEGF-A, VEGF-C; tissue factor (TF); alpha interferon (alphaIFN); TNFalpha, an interleukin, such as IL-1 beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In one embodiment, the heteromultimeric proteins of this invention bind low-density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 1 1) p75 NTR, and 12) caspase-6.

In one embodiment, the heteromultimeric proteins of this invention binds to at least two target molecules selected from the group consisting of: IL-1 alpha and IL-1 beta, IL-12 and IL-18; IL-13 and IL-9; IL-13 and IL-4; IL-13 and IL-5; IL-5 and IL-4; IL-13 and IL-1 beta; IL-13 and IL-25; IL-13 and TARC; IL-13 and MDC; IL-13 and MEF; IL-13 and TGF-43; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1 beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-1 1, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFa and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET. VEGFR and MET receptor, VEGFR and EGFR. HER2 and CD64, HER2 and CD3, HER2 and CD16, HER2 and HER3; EGFR(HERI) and HER2, EGFR and HER3, EGFR and HER4, IL-13 and CD40L, IL4 and CD40L, TNFR1 and IL-1 R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

V. Embodiments

The invention provides additional embodiments as described below. In a first embodiment, a method of producing a heteromultimeric protein is provided, said method comprising: Obtaining a protein A purified first hinge-containing polypeptide; Obtaining a protein A purified second hinge-containing polypeptide; Adjusting the pH of each half-antibody to between 4 and 9; Mixing the first and second hinge-containing polypeptide to obtain a mixed hinge-containing polypeptide pool; Adding a molar excess of a weak reductant to the mixed hinge-containing polypeptide pool; and incubating the mixed hinge-containing polypeptide pool with the weak reducant to form a heteromultimeric protein comprising the first and second hinge-containing polypeptide.

In a second embodiment and according to the first embodiment, the first and second hinge-containing polypeptides can be selected from a half-antibody, immunoadhesin and fragments thereof. In a third embodiment and according to the first embodiment, the first hinge-containing polypeptide is a half-antibody. In a fourth embodiment and according to the first embodiment, the second hinge-containing polypeptide is an Fc component. In a fifth embodiment and according to the third embodiment, the half-antibody comprises a VL domain, a CL domain, a VH domain, a CH1 domain, a hinge domain, a CH2 domain and a CH3 domain. In a sixth embodiment and according to the fifth embodiment, the half-antibody is a single polypeptide chain further comprises a tether wherein said domains are positioned relative to each other in an N-terminal to C-terminal direction as follows: VL-CL-tether-VH-CH1-hinge-CH2-CH3. In a seventh embodiment and according to the first embodiment, the first and second hinge-containing polypeptides are mixed prior to Protein A purification and co-purified over Protein A. In an eighth embodiment and according to the first embodiment, the first and second hinge-containing polypeptides comprise a heteromultimerization domain. In a ninth embodiment and according to the eighth embodiment, the heteromultimerization domain is selected from a knob into hole mutation, leucine zippers, electrostatic, etc. In a tenth embodiment and according to the ninth embodiment, the first hinge-containing polypeptide comprises a knob and the second hinge-containing polypeptide comprises a hole. In an eleventh embodiment and according to the first embodiment, the pH is adjusted after mixing. In a twelfth embodiment and according to the first or eleventh embodiment, the method further comprises adding L-Arginine to a final concentration of between 20 mM to 1M prior to adjusting the pH. In a thirteenth embodiment and according to the first embodiment, the method further comprises incubating the mixed pool at a temperature of between 15° C. and 39° C. for at least 30 minutes. In a fourteenth embodiment and according to the first embodiment, the assembly mixture has an oxidation potential of between −200 to −600 mV, more preferably between −300 to −500 mV, most preferably about −400 mV. In a fifteenth embodiment and according to the first embodiment, the weak reductant is selected from GSH, Beta-MercaptoEthylAmine, cysteine/cysteine, GSH/GSSG, cysteamine/cystamine, glycylcysteine, and beta-mercaptoethanol. In a sixteenth embodiment and according to the first embodiment, the weak reductant is added in 50-600 molar excess. In a seventeenth embodiment and according to the first embodiment, the weak reductant is added prior to mixing. In an eighteenth embodiment and according to the seventeenth embodiment, the addition is done less than one hour prior to mixing. In a nineteenth embodiment and according to the first embodiment, the step of incubating the assembly mixture is done at a temperature between 15° C. and 39° C. in the presence of Polyvinylpyrrolidone (PVP). In a twentieth embodiment and according to the nineteenth embodiment, histidine is added prior to, simultaneously with or after the PVP. In a $21^{st}$ embodiment and according to the nineteenth embodiment, the PVP is added up to 40% (w/v).

In a $22^{nd}$ embodiment, the invention provides a method of producing a bispecific antibody, said method comprising:
  a. Obtaining a protein A purified first half-antibody;
  b. Obtaining a protein A purified second half-antibody;
  c. Adding a L-Arginine solution to each half-antibody;
  d. Adjusting the pH of each half-antibody to between 4 and 9;
  e. Mixing the first and second half-antibody pools to obtain a mixed half-antibody pool,
  f. adding a molar excess of a weak reductant to the mixed half-antibody pool;
  g. incubating the mixed half-antibody pool at a temperature between 15° C. and 39° C. in the presence of PVP, whereby a bispecific antibody comprising the first and second half-antibody is produced.

In a $23^{rd}$ embodiment, the invention provides a method of producing a heteromultimer, said method comprising: (a) Providing an L-arginine containing mixture of at least two different hinge-containing polypeptides, wherein said mixture has a pH of between 7 and 9, (b) adding a molar excess of a weak reductant and (c) incubating the mixture under conditions whereby a heteromultimer is produced.

In a $24^{th}$ embodiment and according to the $22^{nd}$ embodiment, the first half-antibody is a single chain polypeptide comprising (a) A full-length Light chain comprising a VL domain and a CL domain; (b) A tether, (c) A full length Heavy chain comprising a VH domain, CH1 domain, a hinge, a CH2 domain and a CH3 domain; said polypeptide comprising domains of the light and heavy chains positioned relative to each other in an N-terminal to C-terminal direction as follows: VL-CL-CL/VH tether-VH-CH1-hinge-CH2-CH3. In a $25^{th}$ embodiment and according to the $24^{nd}$ embodiment, the single chain polypeptide further comprises a heteromultimerization domain. In a $26^{th}$ embodiment and according to the $25^{th}$ embodiment, the heteromultimerization domain is either a hole (e.g., cavity) or knob (e.g., protuberance). In a $27^{th}$ embodiment and according to the $26^{th}$ embodiment, the second half-antibody comprises a hole when the first half-antibody comprises a knob. In a $28^{th}$ embodiment and according to the $26^{th}$ embodiment, the second half-antibody comprises a knob when the first half-antibody comprises a hole. In a $29^{th}$ embodiment and according to the $24^{th}$ embodiment, the tether comprises GGS repeats. In a $30^{th}$ embodiment and according to the $24^{th}$ embodiment, the tether is 15-50 amino acids.

In a $31^{st}$ embodiment, the invention provides a method of producing a heteromultimeric protein, said method comprising: (a) Obtaining a protein A purified first hinge-containing polypeptide; (b) Obtaining a protein A purified second hinge-containing polypeptide; (c) Adjusting the pH of each hinge-containing polypeptide to between 4 and 9 in the presence of L-Arginine; (d) Mixing the first and second hinge-containing polypeptide to obtain a mixed half-antibody pool, and incubating to form a heteromultimeric protein comprising the first and second hinge-containing polypeptide.

In a $32^{nd}$ embodiment and according to the first or $31^{st}$ embodiment, at least one of the half-antibodies is a single chain polypeptide comprising: (a) A full-length Light chain comprising a VL domain and a CL domain; (b) A tether; (c) A full length Heavy chain comprising a VH domain, CH1 domain, a hinge, a CH2 domain and a CH3 domain.

In a $33^{rd}$ embodiment and according to the first embodiment, the first hinge-containing polypeptide is a single chain polypeptide comprising domains of the light and heavy chains positioned relative to each other in an N-terminal to C-terminal direction as follows: VL-CL-VH-CH1-hinge-CH2-CH3. In a $34^{th}$ embodiment and according to the $33^{rd}$ embodiment, the single polypeptide chain further comprises a tether wherein said domains are positioned relative to each other in an N-terminal to C-terminal direction as follows: VL-CL-tether-VH-CH1-hinge-CH2-CH3.

In a $35^{th}$ embodiment, the invention provides a method of producing a heteromultimer, said method comprising providing an L-arginine containing a mixture of hinge-containing polypeptides, said mixture having a pH of between 4 and 9, adding a weak reductant and incubating under conditions so as to produce a heteromultimer.

In a $36^{th}$ embodiment, the invention provides a host cell that has been engineered to express a half-antibody wherein said half-antibody is a single chain polypeptide comprising a tether, a VL domain, a CL domain, a VH domain, a CH1 domain, a hinge domain, a CH2 domain and a CH3 domain wherein said domains are positioned relative to each other in an N-terminal to C-terminal direction as follows: VL-CL-tether-VH-CH1-hinge-CH2-CH3. In a $37^{th}$ embodiment and according to the $36^{th}$ embodiment, the single polypeptide chain further comprises a heterodimerization domain. In a $38^{th}$ embodiment and according to the $36^{th}$ or the $37^{th}$ embodiment, the host cell is selected from prokaryotic cells, eukaryotic cells, mammalian cells or plant cells. In a 39$^{th}$ embodiment and according to the 38$^{th}$ embodiment, the host cell is a prokaryotic cell. In a 40$^{th}$ embodiment and according to the 39$^{th}$ embodiment, the prokaryotic cell is an *E. coli* cell. In a 41$^{st}$ embodiment and according to the 40$^{th}$ embodiment, the *E. coli* cell is Ipp deficient. In a 42$^{nd}$ embodiment and according to the 38$^{th}$ embodiment, the host cell is a mammalian cell. In a 43$^{rd}$ embodiment and according to the 41$^{st}$ embodiment, the mammalian cell is a CHO cell. In a 44$^{th}$ embodiment and according to the 36$^{th}$ or 37$^{th}$ embodiment, the host cell comprises a vector encoding the single chain half-antibody. In a 45$^{th}$ embodiment and according to the 36$^{th}$ or 37$^{th}$ embodiment, the half-antibody further comprises a heterodimerization domain. In a 46$^{th}$ embodiment and according to the 45$^{th}$ embodiment, the heterodimerization domain is selected from a knob, a hole, one or more charged amino acids within the interface that are electrostatically unfavorable to homodimer formation but electrostatically favorable to heterodimer formation, one or more amino acids are altered to enhance intramolecular ionic interactions, a coiled coil and a leucine zipper.

In a 47$^{th}$ embodiment, the invention provides a mixture of host cells comprising a first host cell engineered to express a first single chain half-antibody and a second host cell engineered to express an Fc component. In a 48$^{th}$ embodiment and according to the 36$^{th}$ embodiment, the half-antibody produced by a host cell comprises a heterodimerization domain.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein.

Example 1: Expression & Purification

This example illustrates the expression and purification of half-antibodies.

Exemplary methods of construction and expression of half-antibodies in *E. coli* can be found for example in co-pending application U.S. 2011/0287009, which is incorporated herein by reference in its entirety. It is within the ability of one of skill in the art to modify and adjust the culture and expression conditions.

Expression of Half-Antibodies in *E. coli* Cells

Construction of Expression Plasmids

Both the heavy and light chain DNA coding sequences were cloned into an expression plasmid that contained separate promoter elements for each of the sequences and antibiotic resistance for selection of bacterial cells that contain the expression plasmid. The vector constructs also encode the heat-stable enterotoxin II (STII) secretion signal (Picken et al., 1983, Infect. Immun. 42:269-275, and Lee et al., 1983, Infect. Immun. 42:264-268) for the export of the antibody polypeptides into the periplasmic space of the bacterial cell. Transcription of each chain is controlled by the phoA promoter (Kikuchi et al., 1981, Nucleic Acids Res., 9:5671-5678) and translational control is provided by previously described STII signal sequence variants of measured relative translational strength, which contain silent codon changes in the translation initiation region (TIR) (Simmons and Yansura, 1996, Nature Biotechnol. 14:629-634 and Simmons et al., 2002, J. Immunol. Methods, 263:133-147).

Each half-antibody had either a knob (protuberance) or a hole (cavity) engineered into the heavy chain as described in U.S. Pat. No. 7,642,228. Briefly, a CH3 knob mutant was generated first. A library of CH3 hole mutants was then created by randomizing residues 366, 368 and 407 that are in proximity to the knob on the partner CH3 domain. In the following examples, the knob mutation was T366W, and the hole had mutations T366S, L368A and Y407V in an IgG1 or IgG4 backbone. Equivalent mutations in other immunoglobulin isotypes can be made by one skilled in the art. Further, the skilled artisan will readily appreciate that it is preferred that the two half-antibodies used for the bispecific be the same isotype.

Expression and Purification

Half-antibodies containing either the knob or hole mutations were generated in separate cultures by expressing the heavy and light chains constructs in a bacterial host cell, e.g., *E. coli*. The expression plasmids were introduced into *E. coli* host strains 33D3 (Ridgway et al. (1999) 59 (11): 2718) or 64B4 (W3110.DELTA.fhuA .DELTA.phoA ilvG+.DELTA.prc spr43H1.DELTA.degP .DELTA.manA lacI.sup.q .DELTA.ompT) and transformants were selected on carbenicillin containing LB plates. Transformants were then used to inoculate an LB starter culture containing carbenicillin, and this was grown overnight with shaking at 30° C. The starter culture was diluted 100× into a phosphate limiting media C.R.A.P. (Simmons et al., 2002, J. Immunol. Methods, 263:133-147) containing carbenicillin, and the culture was grown for 24 hours with shaking at 30° C. The cultures were centrifuged, and the cell pellets frozen until the start of antibody purification. The pellets were thawed and resuspended in an extraction buffer containing 25 mM Tris-base adjusted to pH 7.5 with hydrochloric acid, 125 mM NaCl and 5 mM EDTA (TEB or Tris Extraction Buffer) with a volume to weight ratio of 100 mL TEB per 5 grams of cell pellet, and extracted by disrupting the cells using microfluidics by passing the resuspended mixture through a Microfluidics Corporation model 110F microfluidizer (Newton, Mass.) three times. The bacterial cell extract was then clarified by centrifugation for 20 minutes at 15,000×g and the supernatant collected and filtered through a 0.22 micron acetate filter prior to purification.

Each half-antibody was purified separately by Protein A affinity chromatography. Clarified cell extracts from the knob half-antibody were loaded onto a 1 mL HiTrap MAB-SELECT SURE™ column from GE Healthcare (Pistcataway, N.J.) at 2 mL/min. After loading the column was washed with 10 column volumes (CV) of 40 mM sodium citrate, pH 6.0, 125 mM sodium chloride, and 5 mM EDTA followed by 5 column volumes of 20 mM sodium citrate at pH 6.0 to facilitate capture by the cation exchange column. The affinity captured half-antibodies were eluted with 10 column volumes (CV) of 0.2 mM acetic acid (pH 2-3).

Expression of Half-Antibodies in CHO Cells
Construction of Expression Plasmids.

Both heavy chain and light chain cDNAs were under the control of Cytomegalovirus immediate-early gene promoter and enhancer (CMV). Each CMV transcriptional start site is followed by splice donor and acceptor sequences, which define introns that are removed from the final transcripts (Lucas et al., High-level production of recombinant proteins in CHO cells using a dicistronic DHFR intron expression vector. Nucl. Acid Res. (1996) 24:1774-9). The glutamine synthetase (GS) enzyme was used as the selection marker for stable cell line development (Sanders et al., Amplification and cloning of the Chinese hamster glutamine synthetase gene. The EMBO J (1984) 3:65-71) and was under the control of SV40 early promoter and enhancer.

Cell Culture.

CHO cells were cultured in a proprietary DMEM/F12-based medium in shake flask vessels at 37° C. and 5% $CO_2$. Cells were passaged with a seeding density of $3 \times 10^5$/mL, every three to four days.

Stable Transfection.

CHO cells were transfected using lipofectamine 2000 CD according to the manufacturer's recommendation (Invitrogen, Carlsbad, Calif.). Transfected cells were centrifuged and seeded into DMEM/F-12-based selective (glutamine-free) medium with various concentrations of methionine sulfoximine (MSX). About three weeks after seeding, individual colonies were picked into 96-well plates. Picked colonies were evaluated for antibody production by taking the supernatant for ELISA analysis. Top clones were scaled-up and evaluated based on antibody titers, favorable metabolism (mainly lactate consumption), and acceptable product quality attributes.

Expression:

Each half antibody was expressed in CHO cells. 2L cultures were grown and harvested.

Purification of Half-Antibodies.

Each half antibody was captured on a MABSELECT SURE™ column. The column was then washed with 4 column volumes (CV) of the following buffers: an equilibration buffer consisting of 50 mM TRIS pH 8.0, 150 mM NaCl, and a wash buffer consisting of 0.4M Potassium Phosphate pH 7.0. Each arm was eluted into 0.15 M Sodium Acetate at pH 2.9.

The above described methods of expression and purification of half-antibodies are generally applicable to IgG of different isotypes.

Example 2: Solubilizer & pH Hold

The following example details how the incubation of half-antibodies at an intermediate pH drove conformation shift and increased assembly efficiency, and how the addition of a solubilizer such as arginine and histidine reduced the intermediate pH-induced precipitation of half-antibodies.

Half-antibody protein A pools are inherently unstable due to the exposed inner surface of the CH2 and CH3 domains which are likely to contain hydrophobic patches which are normally in the non-solvent exposed surface of an antibody. Thus, when adjusted to pH greater than 4 half-antibody protein A pools tend to precipitate. The instant inventors discovered that with a minimum concentration of L-Arginine present (in certain examples ≥50 mM) the half antibody was stabilized and remained in solution upon pH adjustment. This addition of a solubilizer such as arginine kept the half antibody in solution, reduced turbidity upon pH adjustment, and increased bispecific assembly yield. See FIG. 3. Arginine also protected bispecific half antibodies and purified bispecific from forming aggregation during freezing. Similar precipitation-reducing effect was also seen in histidine.

The recovered protein from the Protein A columns in Example 1 were used as the starting material for this example.

L-Arginine (1M, pH 9) was added to the Protein A purified protein to a final concentration of 50-600 mM. The solution was subsequently titrated to a higher pH using 1.5M Tris Base, pH 11, as needed. The step of elevating to intermediate pH after acidic elution from the Protein A column is referred to as intermediate pH hold.

Figure 2A:
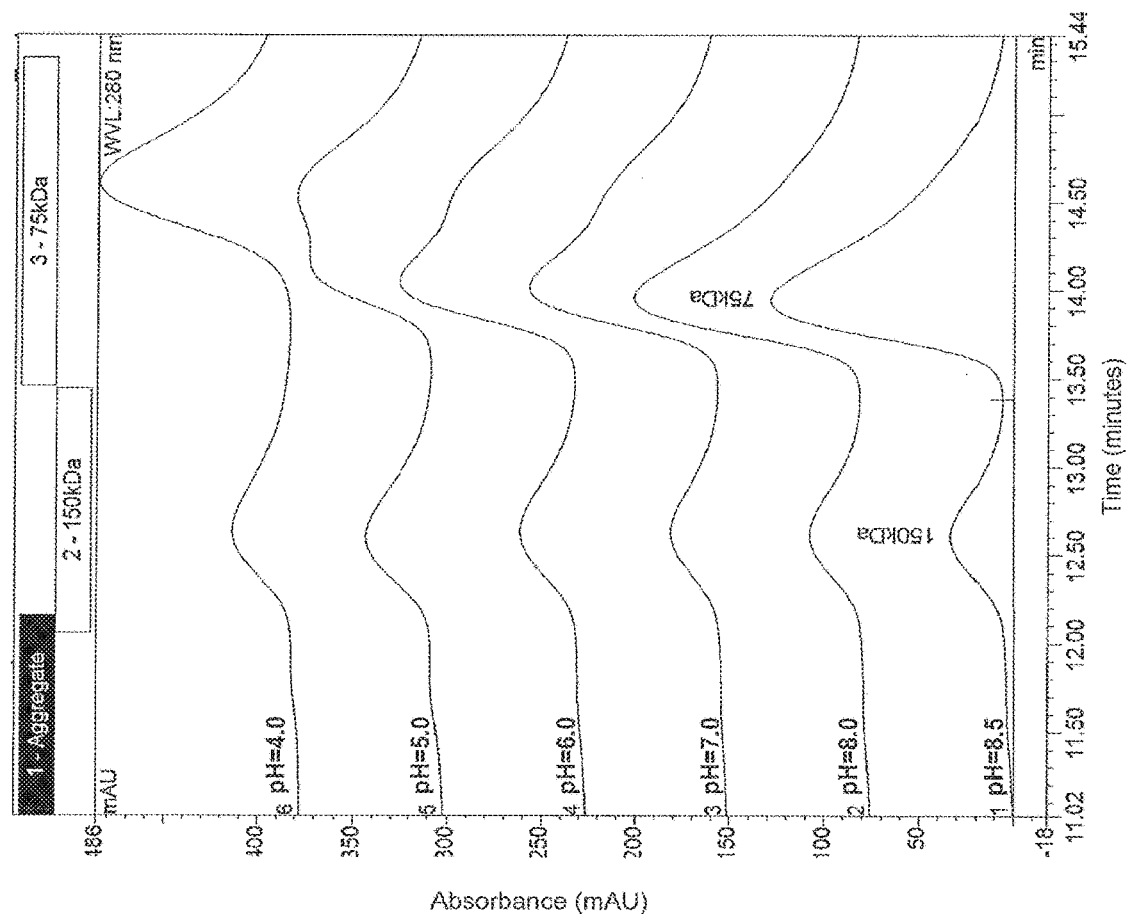
FIGS. 2A-B show composite size exclusion chromatograms demonstrating the effects of pH on the conformation shift of half-antibodies.
Figure 2B:
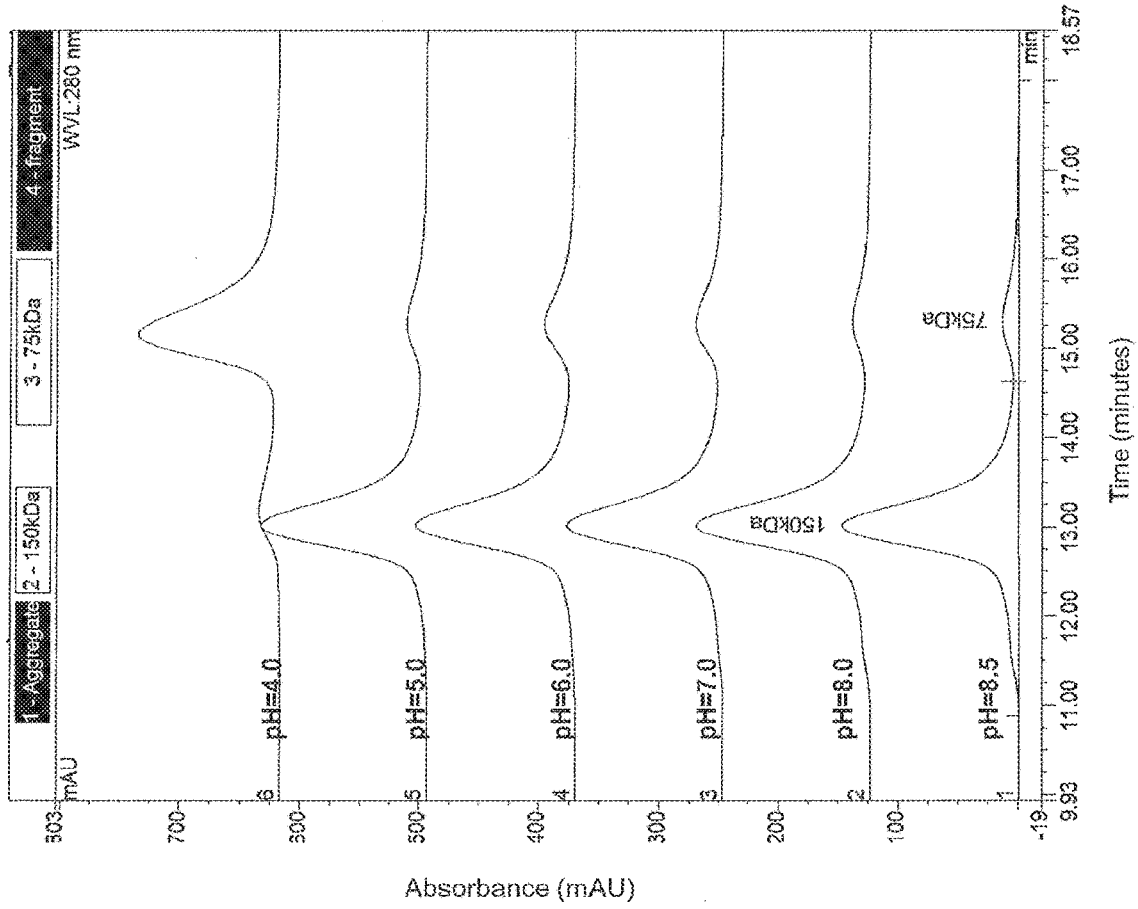

Due to the knob and hole mutations in the CH3 domain bispecific antibodies have different degrees of flexibility compared to standard antibodies. As a result of this unique flexibility and the exposed inner surfaces of the CH2 and CH3 domains half antibodies appeared to undergo conformational shifts upon pH adjustment. See FIG. 2.

In this experiment, knobs underwent a shift from monomer to non-covalently linked homodimer when the pH was adjusted to a pH greater than 4. See FIG. 2B. Holes underwent a conformation shift from a smaller hydrodynamic radius to a larger hydrodynamic radius based on Size Exclusion Chromatography retention time. The shift began to occur at pH 5 and pH a 7 drove the shift to completion. See FIG. 2A.

Size exclusion chromatography (SEC) for the determination of the aggregation and oligomeric state of antibodies was performed by HPLC chromatography. Briefly, Protein A purified antibodies were applied to a Tosoh TSKgel SW2000 column on an Agilent HPLC 1200 system. Protein (IgG1 half-antibody produced in *E. coli*) was eluted with 0.2M K3PO4 0.25M KCl pH 6.2 at a flow rate of 0.5 mL/min. The eluted protein was quantified by UV absorbance and integration of peak areas. See FIGS. 2 A & B. This shift may represent a folding intermediate that was induced by pH change due to the higher flexibility of the half antibody, especially knob and hole half-antibodies with mutations in the CH3 domain.

Figure 3A:
FIGS. 3A-3B depict the results showing that a solubilizer such as arginine (FIGS. 3A and B) or histidine hydrochloride (FIG. 3B) reduced intermediate pH-induced precipitation of knob half-antibodies.

The intermediate pH hold, however, may result in precipitation of half-antibodies. As shown in FIG. 3A, the presence of arginine reduced pH-induced turbidity of the Protein A purified IgG1 knob half-antibodies. In this experiment, 1M arginine was used to titrate the pH in the *E. coli* produced-IgG1 half-antibody Protein A pools. The final arginine concentration was about 50 mM when the pH was titrated to 5.5, about 200 mM at pH 7.5, and about 400 mM at pH 8.5 (see FIG. 3A). The presence of arginine also improved assembly yield of the knob-into-hole bispecific antibody by 15% (data not shown).

Similarly, histidine was able to reduce pH-induced turbidity due to precipitation. A "knob" IgG1 half-antibody was purified from *E. coli* homogenate on a MABSELECT SURE™ column, resulting in a Protein A pool with a concentration of 12 g/L half-antibody. One-fourth volume of Arginine-Hydrochloride or Histidine-Hydrochloride was added to a final additive concentration of 200 mM, with an equivalent volume of purified water added for the "None" control. Sample pH was increased using concentrated Sodium Hydroxide (50% w/v NaOH solution, or 19.1 N) added dropwise, and data points were recorded. The pH was measured using an Orion Ross 81-03 microprobe. Turbidity of solution was measured using a Hach 2100 laboratory turbidity meter.

Figure 3B:
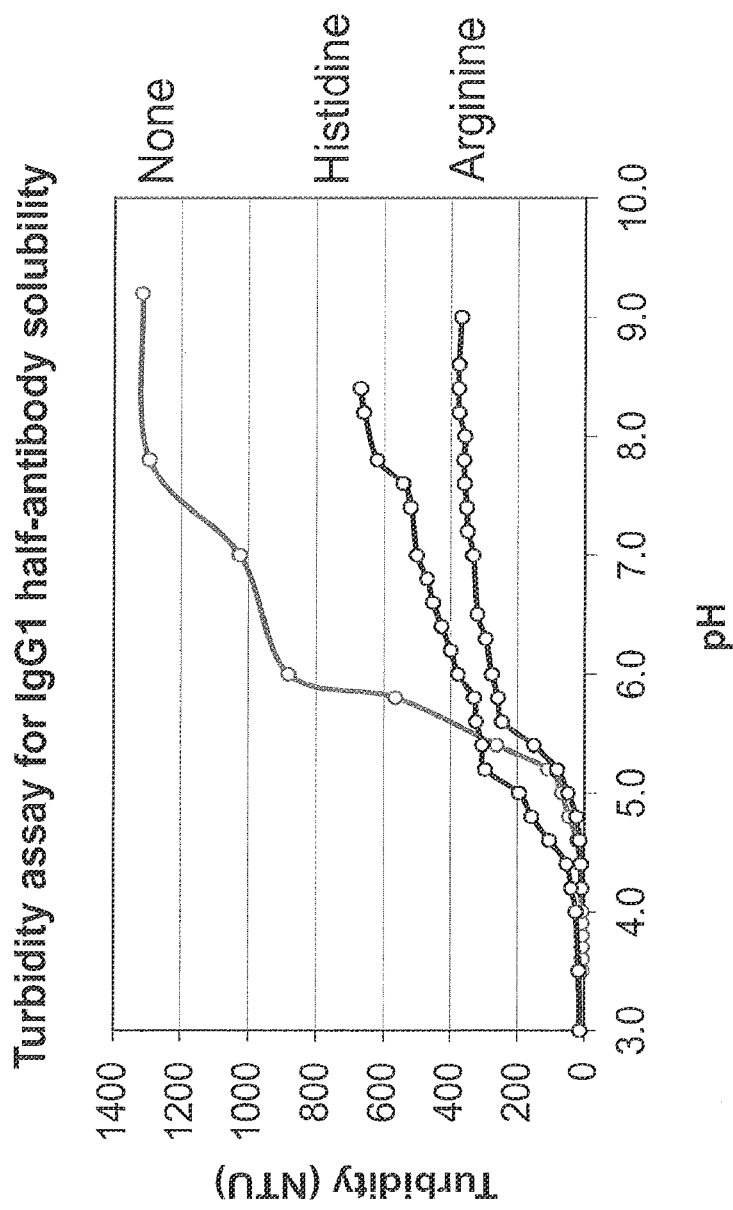

The data in FIG. 3B showed that both arginine (200 mM) and histidine (200 mM) reduced pH-induced precipitation in IgG1 isolated from *E. coli*. In summary, intermediate pH induced half-antibody conformation shift in favor of bispecific assembly, and a solubilizer added to the intermediate pH hold step reduced pH-induced precipitation.

Example 3: Reduction

The following example details how the use of a reducing condition decreases aggregation resulting in more formation of the desired heteromultimer, e.g., a bispecific antibody. For example, glutathione added to an assembly mixture creates a weakly reducing condition that is advantageous for knob-into-hole bispecific assembly. Other reductants in a similar class such as BMEA (Beta-MercaptoEthylAmine) may have a similar effect.

Aggregation can occur during assembly of the knob and hole half antibodies to form bispecific. Increasing glutathione levels minimize the amount of aggregation during assembly. In contrast, strong reductants such as DTT at high concentrations may sometimes increase aggregation. Without being limited to specific mechanisms, instead of reducing the disulfide bonds permanently glutathione seems to shuffle disulfides acting as a catalyst for proper disulfide formation. With glutathione assemblies a buffer exchange is not required in order to form the hinge region disulfides in the bispecific product of interest, as is required for reoxidation when using a strong reductant. Addition of a chemical re-oxidant is not required either when a weak reductant such as glutathione is used.

Glutathione concentrations can be expressed in terms of molarity or in terms of molar ratio with respect to the amount of the hinge-containing polypeptides or half-antibodies present in the assembly mixture. Using a target molar ratio of reductant controls for the protein concentration in the assembly mixture; this prevents over reducing or under reducing as a result of variable protein concentrations.

Figure 4A:
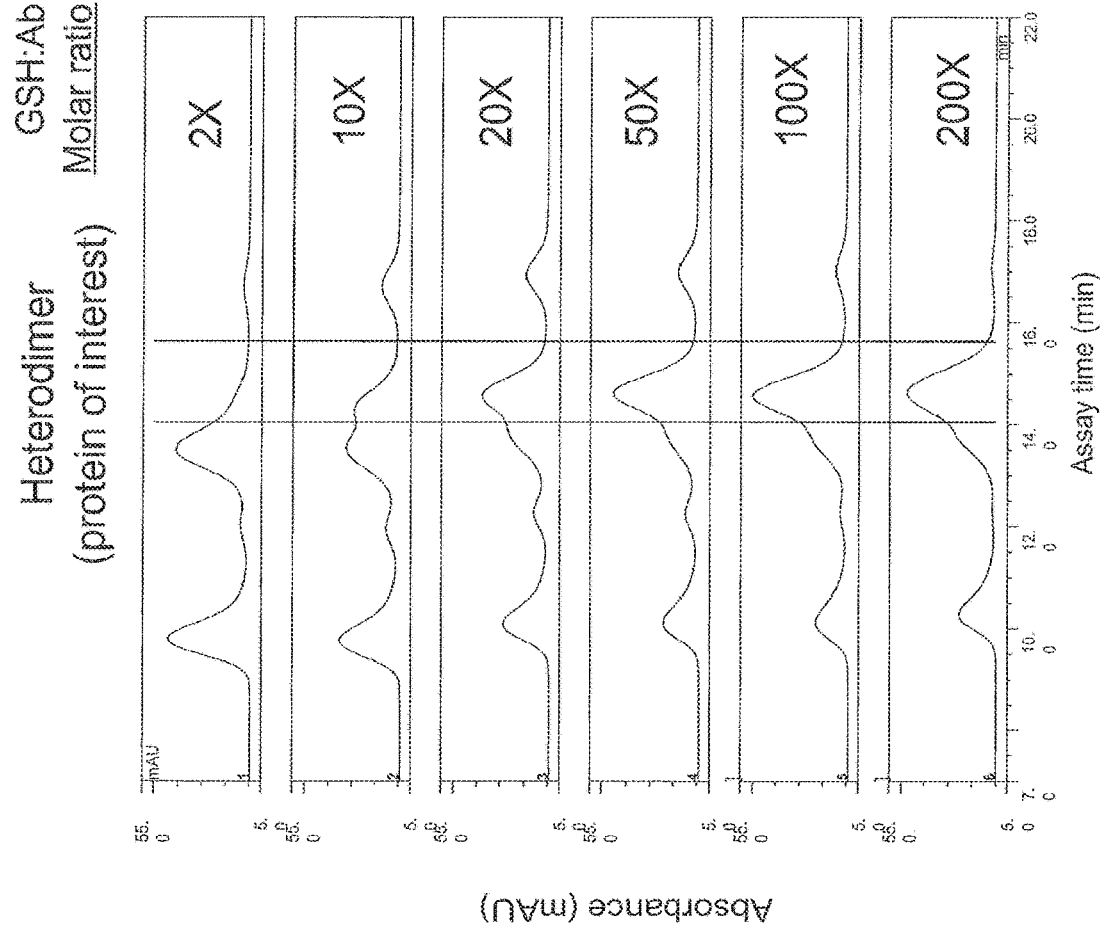
FIGS. 4A-B show composite chromatograms demonstrating the effect of a reductant such as glutathione on aggregation and bispecific antibody assembly. Glutathione is added in 2-200× molar excess. Reference is made to Example 3.

In this example, glutathione was added to the mixed half-antibodies from 2 to 200× molar excess. The samples were incubated at room temperature for 46 hours. In the RP-HPLC (reversed phase-high performance liquid chromatography) all samples were diluted with 0.1% Trifluoroacetic Acid to a maximum concentration of 1.0 mg/ml. The protein concentration was determined by photometric measurements at 280 nm. Four samples of 0.1% Trifluoroacetic Acid were injected prior to the sample analysis. This ensured that the column was completely equilibrated. Protein A purified *E coli*-produced IgG1 half-antibodies were applied to a Poros R2/20 2.1 mmD×20 mmL on an Agilent HPLC 1200 system. Protein was eluted with a linear gradient of 38-49% Buffer A to 0.09% Trifluoroacetic Acid 80% Acetonitrile (Buffer B) in 20 minutes at a flow rate of 0.5 mL/min. The eluted protein was quantified by UV absorbance and integration of peak areas. As shown in FIG. 4A, the level of bispecific formation increased with increased glutathione:Ab molar ratio. See FIG. 4A.

Size exclusion chromatography (SEC) for the determination of the aggregation and oligomeric state of antibodies was performed. Briefly, Protein A purified *E coli*-produced IgG1 half-antibodies were applied to a Tosoh TSKgel SW2000 column on an Agilent HPLC 1200 system. Protein was eluted with 0.2M K3PO4 0.25M KCl pH 6.2 at a flow rate of 0.5 mL/min. The eluted protein was quantified by UV absorbance and integration of peak areas. The 150 kD peak observed was confirmed to be due to the formation of bispecific antibody. See FIG. 4B.

Figure 4B:
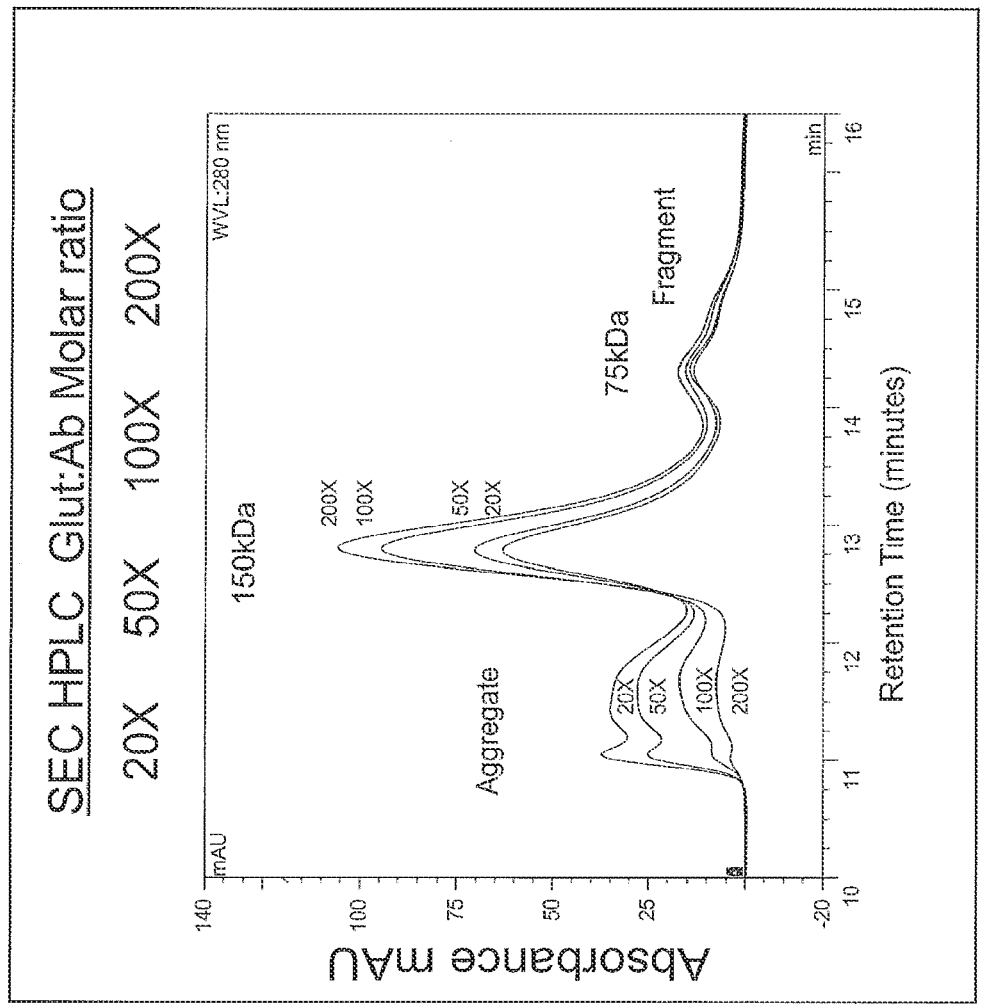

As can be seen there is a shift in peaks from the unwanted monomers (i.e., half-antibodies, either knob or hole) and homodimers to the heteromultimer, i.e., a bispecific antibody (FIGS. 4A and B). In summary, the data show that increasing molar ratio of glutathione to half-antibodies reduced aggregation and improved bispecific formation (FIG. 4B).

Example 4: Temperature

This example illustrates the effect of temperature on the stability of half-antibodies and the assembly of the heteromultimer.

Figure 5A:
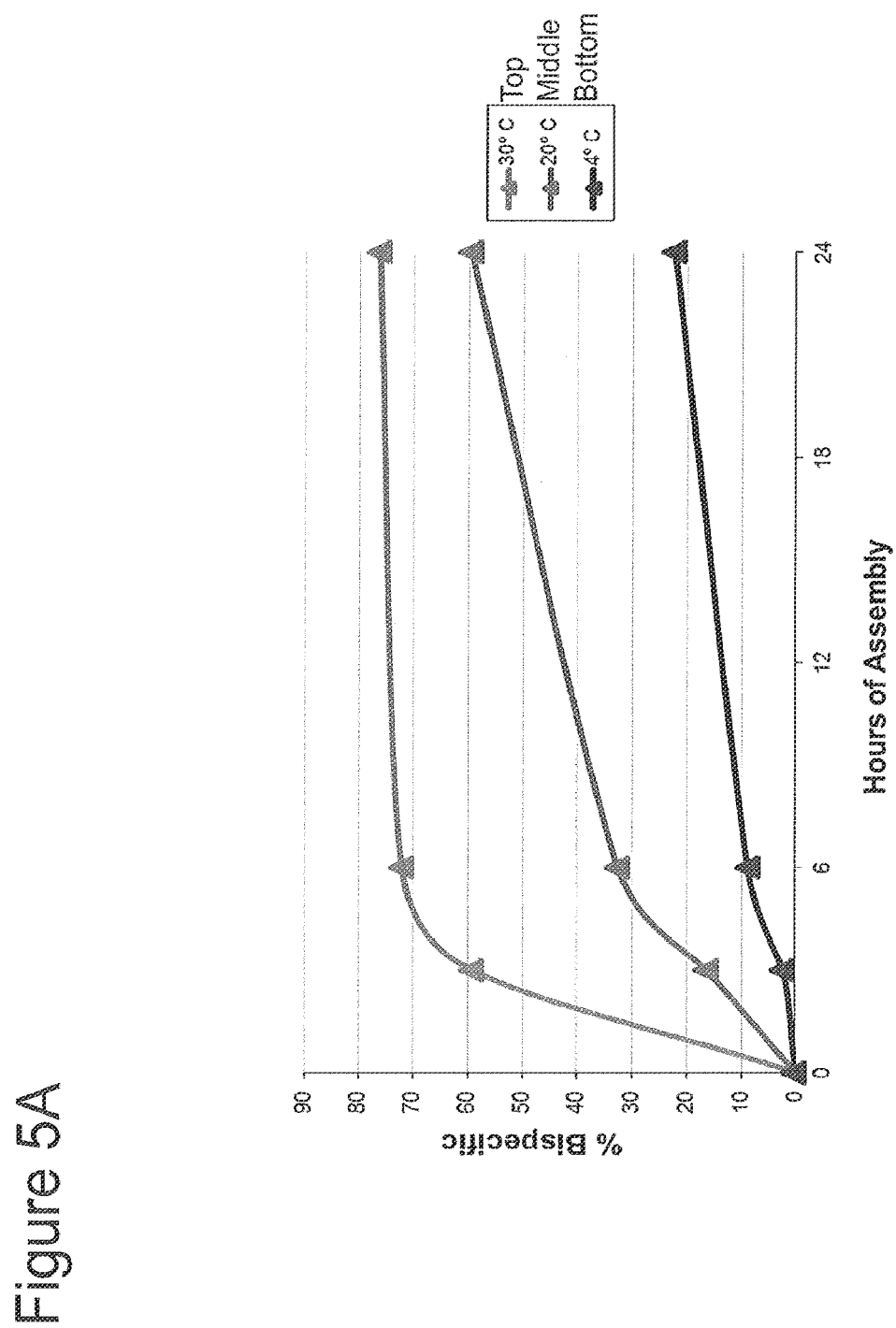
FIG. 5A is a graph illustrating the effect of temperature on the rate of IgG1 bispecific antibody formation (assembly).

The temperature of the solution of the half-antibodies had a dramatic impact on the rate of assembly. One example of enhanced assembly of *E. coli*-produced IgG1 half-antibodies at higher temperature is shown in FIG. 5A.

Figure 5B:
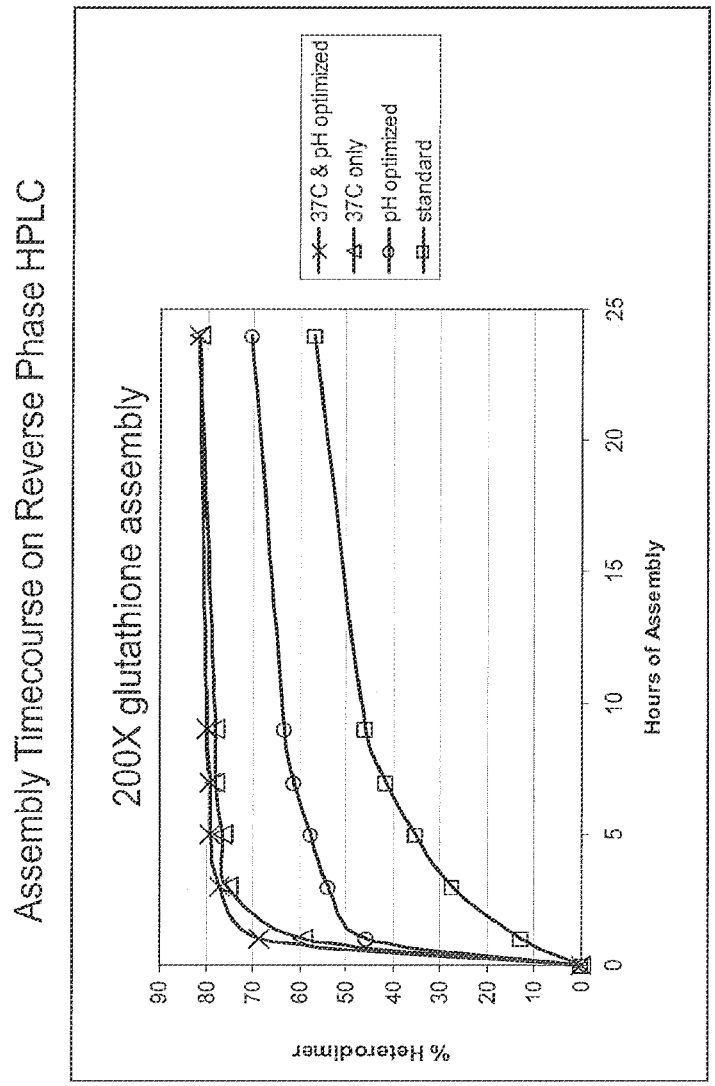
FIG. 5B shows that increased temperature promoted assembly of knob-into-hole bispecific IgG1 antibody in the presence of 200× molar excess of glutathione with or without pH hold as analyzed by reverse phase chromatography.

Another example showing the effect of temperature on bispecific assembly is shown in FIG. 5B. In this experiment, two IgG1 half-antibodies were produced in *E. coli* and purified over Protein A as described in Example 1. The half antibodies were combined and divided into four aliquots for testing bispecific assembly under different conditions with or without heating and/or intermediate pH hold.

As shown in FIG. 5B, a 200 molar excess of glutathione under varying conditions enhanced the rate of bispecific IgG1 antibody formation. The control conditions (room temperature, about 20° C., half-antibody was kept at pH 4, no intermediate pH hold), allowed assembly of the bispecific albeit at a slower rate. Holding the Protein A purified half-antibodies at an intermediate pH (pH 5 for knob half-antibody; pH 7 for hole half-antibody) for 16 hours at room temperature improved the rate of bispecific antibody formation without going to a higher temperature (assembly mixture was at pH 8.5 in "pH optimized" in FIG. 5B). Increasing temperature to 37° C. without an intermediate pH holding step increased the rate of bispecific antibody assembly over the control and it was faster relative to a pH holding step and the assembly done at room temperature. The fastest assembly rate, however, was seen when the Protein A purified half-antibodies were held at an intermediate pH (as above), then assembled at pH 8.5 at elevated temperature (i.e., 37° C.). Under this condition, about 80% of bispecific assembly was achieved in only about 6 hours (FIG. 5B). In summary, the overall assembly rate was increased by heating, and the pH hold and heating had a synergistic effect on assembly.

Figure 6A:
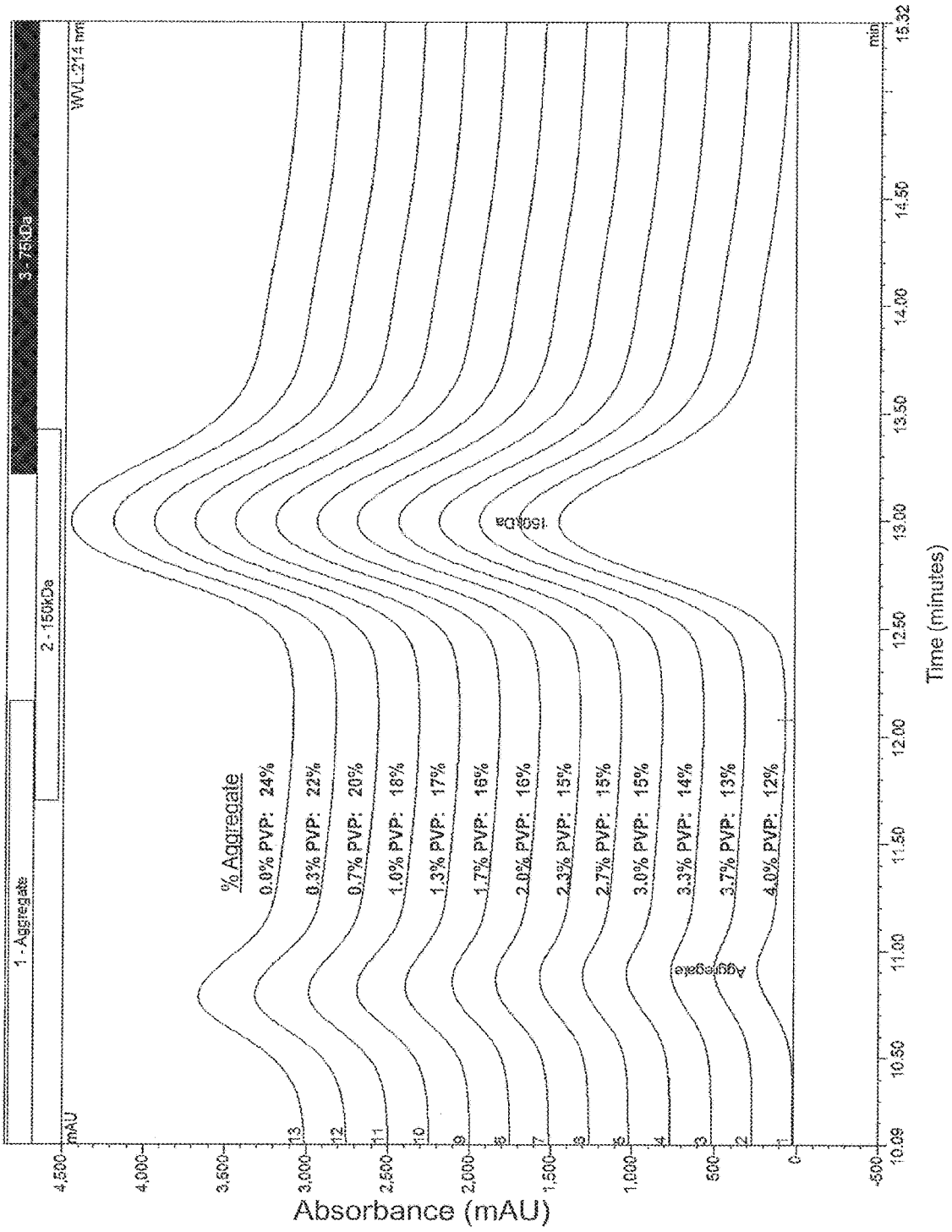
FIG. 6A illustrates the effect of a stabilizer such as PVP on stabilizing the formed bispecific antibody and reduction in aggregate formation.
Figure 6B:
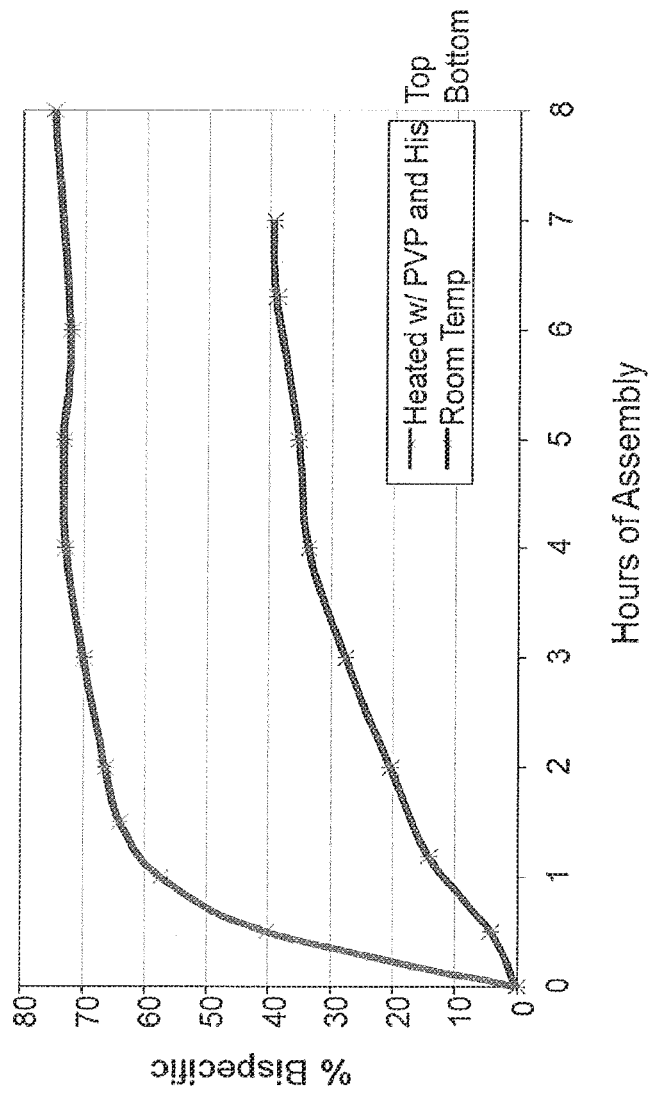
FIG. 6B shows that PVP and histidine at elevated temperature promoted assembly of knob-into-hole bispecific IgG4 antibody as analyzed by reverse phase chromatography. Bottom curve: room temperature assembly with 300× Glutathione:Ab ratio, pH=8.5, ~400 mM Arginine; top curve: heated assembly with 200× Glutathione:Ab ratio, pH=8.0, 4% PVP, 50 mM Arginine, 100 mM Histidine at 35° C.

Heat-enhanced assembly was also seen in IgG4 bispecific antibody. The results of FIG. 6B show that in the presence of PVP and histidine, heated IgG4 half-antibodies produced by *E. coli* culture reached similar assembly results as the assembly of *E. coli*-produced IgG1 half-antibodies. The amount of bispecific was analyzed using reverse phase HPLC as described above. Taken together, the data show that heating facilitated bi-specific formation.

Example 5: Stabilizers

The following example details how stabilizers can reduce aggregation as a result of heating and/or elevated pH during assembly and/or intermediate pH hold.

Polyvinylpyrrolidone (PVP) is a water soluble uncharged polymer with a pyrrolidone group. PVP reduced aggregation during heated assembly. Without being limited to specific mechanisms, PVP can act to stabilize a folding intermediate of the bispecific or protect the half antibodies from aggregation likely by interacting with the hydrophobic patches of the bispecific.

The effect of PVP on aggregate formation was analyzed using SEC under the conditions as described in Example 3. Adding PVP minimized the high molecular weight species (HMWS) present in the assembled pool to 12% HMWS with 4% PVP (w/v) compared to 4% NMWS without adding PVP. See FIG. 6A. All samples were *E. coli*-produced IgG1 heated in the presence of 200 mM arginine.

Next, the assembly of IgG4 bispecific antibody was tested. As shown in FIG. 6B, heated assembly in the presence of PVP and histidine greatly improved *E. coli*-produced IgG4 bispecific assembly to levels similar to the heated assembly of IgG1 produced by *E. coli* shown in FIG. 5A. Arginine was present in both the heated sample and the room temperature sample as a solubilizer and a pH titrant. In addition to PVP, another stabilizer Histidine was added before the heated intermediate pH hold step to stabilize half-antibody during this step. The results show that both PVP and histidine improved IgG4 bispecific assembly to levels similar to IgG1 bispecific assembly (compare FIGS. 6B with 5B).

Figure 6C:
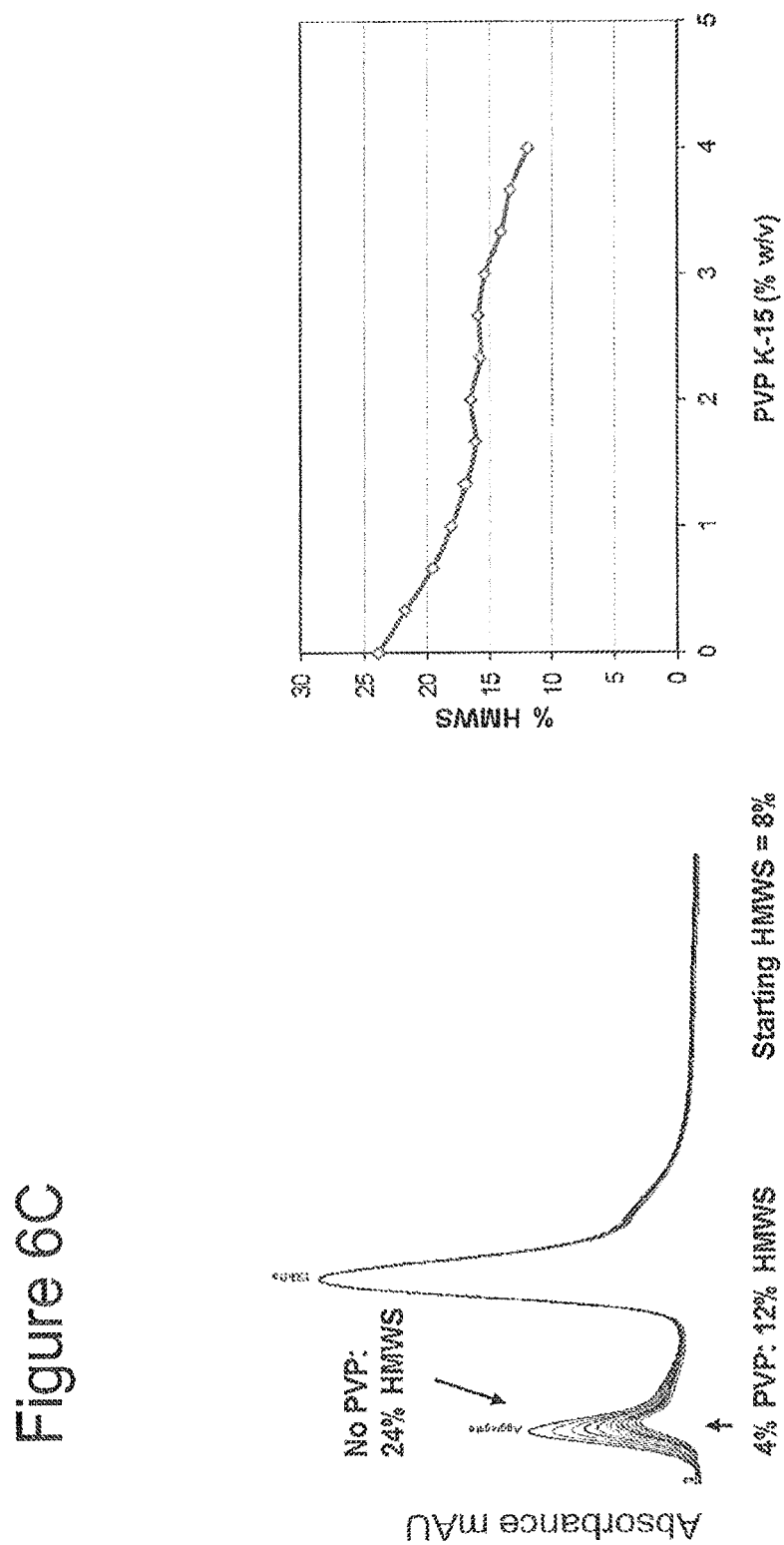
FIG. 6C demonstrates that PVP reduced aggregation of IgG4 knob-into-hole bispecific antibody during heated assembly at 37° C. and pH 8 for 6 hours. Reference is made to Example 5.

FIG. 6C presents another example in which PVP minimized the formation of HMWS during heated assembly of an IgG4 bispecific antibody.

Heating the Half-antibody Protein A pools accelerated the conformation shifts of the half antibodies upon incubation at an intermediate pH. But heating can cause aggregation especially for IgG4 knob and hole bispecific antibodies assembly from IgG4 half-antibodies produced in *E. coli*, Thus, additional solubilizer and/or stabilizers were added when IgG4 half-antibodies were heated during assembly.

Figure 7:
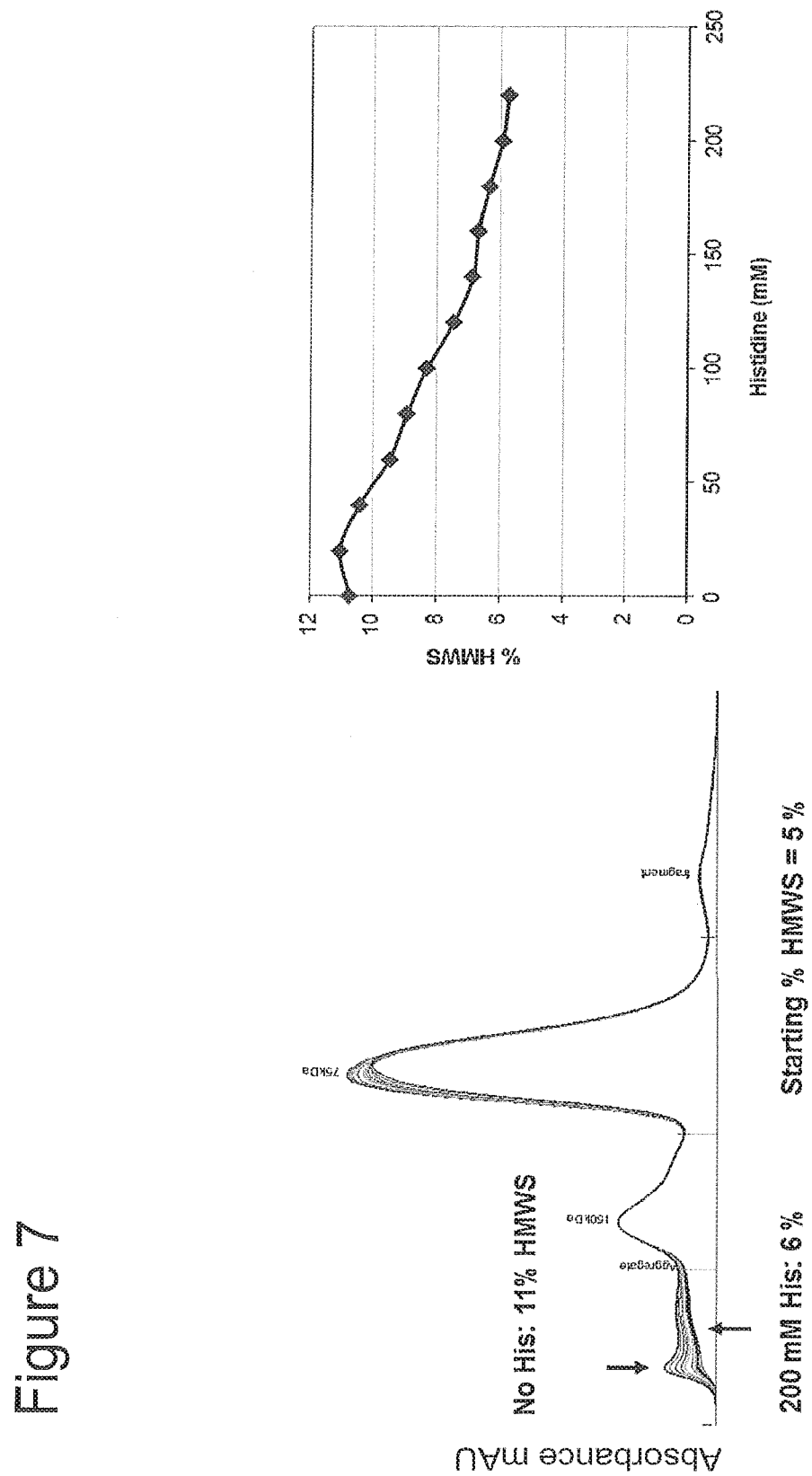
FIG. 7 illustrates that histidine reduced heat-induced aggregation of IgG4 hole half-antibodies at 37° C. and pH 8 for 3 hours.

Conformation shift of *E. coli* IgG4 hole half-antibody was detected after 48 hours of incubation at room temperature. When the IgG4 hole half-antibodies were incubated at 37° C., conformation shift was detected in about three hours (data not shown). Heating, however, led to increase in aggregation as determined by SEC. See FIG. 7, left panel. In this experiment, histidine was added during the heated intermediate pH hold step to test its effect on reducing aggregation of half-antibodies. As shown in FIG. 7, the presence of histidine during heating minimized the level of aggregation from 11% high molecular weight species (HMWS, no histidine) to 6% HMWS (200 mM histidine), without affecting conformation shift of the half antibodies. The results thus show that a stabilizer reduced aggregate formation during both assembly of bi-specific antibodies as well as intermediate pH hold of half-antibodies.

Example 6—Assembly

This example provides protocols for two exemplary immunoglobulin isotypes, i.e., IgG1 and IgG4. The half-antibodies were produced in one of two different host cells, i.e., either *E. coli* or CHO. It is understood that the methods described herein can be applied to other antibody isotypes produced in the same or other sources. It is within the ability of one skilled in the art to modify the protocols by routine experimentation based on the knowledge in the art and the teachings disclosed in the instant application.

Further, it is understood that formation of an antibody comprising a half-antibody produced in a first host cell (e.g., CHO) may be assembled with a complementary half-antibody produced in a second host cell (e.g., *E. coli*) (data not shown). Thus, for example, a knob half-antibody produced in CHO may be assembled with a hole half-antibody produced in *E. coli* or vice versa.

All four of the assembly procedures described in this example resulted in assemblies that plateaued after 4 hours and produced less than 10% aggregate and minimal aggregation during assembly.

A. IgG1 from *E. coli*:

Conformation Change of Half-Antibodies:

If the protein A pools were at a pH less than 7, the pH of both half-antibody pools was adjusted to pH 7 using 1M Arginine (pH 9), and both pools incubated at 37° C. for 3 hours. Alternatively, the pools were incubated at room temperature for 48 hours. If the pools were already at pH 7 for 48 hours or more, skip this step. The amount of Arginine added to get the solution to pH 7 was quantified.

The (still-warm) pools were combined, and the pH adjusted to pH 8.5 using 1M Arginine (pH 9). The amount of Arginine added at this stage was quantified.

2M Arginine (pH 8.5) was added until final concentration of Arginine was 0.5 M.

200 mM reduced glutathione (GSH) in 0.5 M Arginine (final pH 8.5) was added until the GSH:Ab ratio was 200× (ex: add 6.88 µL of the glutathione solution for each mg of half-antibody).

The glutathione half-antibody solution was incubated at 37° C. for 4 hours to allow the half-antibodies to assemble into a bispecific antibody.

B. IgG1 from CHO:

Assembled as described above for *E. coli*. The pH may not need to be raised to pH 7 or above for the intermediate pH hold. Assembly time after the addition of glutathione may reach completion after 2 hours.

C. IgG4 from CHO:

Assembled under the same conditions as above (IgG1 from CHO). Histidine and PVP may not be required.

D. IgG4 from *E. coli*:

Assembling IgG4 from *E. coli* using the above protocols resulted in high, i.e., ~35%, aggregate levels. This necessitated modifications of assembly conditions:

It was determined that the Protein A pool composition containing 0.2 M histidine and 50 mM Arginine yielded acceptable results (data not shown). Thus, several ways to provide the end result were investigated and determined to provide acceptable results.

A first method used altered elution (pH 3) and wash buffers (pH 7) during Protein A purification to contain 0.2 M His & 50 mM Arg. This resulted in the final Protein A pool containing 0.2M His and 50 mM Arg, pH 4, that was then titrated to pH 8 using 1.5M Tris base (pH 11).

A second alternative method utilized a 0.8M solution of Histidine HCl (which has a solubility of 0.8 M). A one third-volume of the Histidine HCl was added to the Protein A pool(s) to reach a final concentration of 0.2M His. Then a ¹⁄₄₀th volume of 2M Arg was added.

A third alternative method was to Buffer-exchange the Protein A pools into a 0.2 M His & 50 mM Arg buffer (preferably at pH 8).

A final alternative method was to add Histidine directly to the Protein A pool(s) (31.03 g/L), then add ¹⁄₄₀th volume of 2M Arg.

A one quarter-volume of a 20% w/v solution of Spectrum PVP K-15 in 0.2M Histidine and 50 mM Arg was added to the Protein A pool(s).

It was noted that PVP also minimized aggregation during assembly for IgG1 under low glutathione conditions.

Conformation change of half-antibodies: The pH of the protein A pool(s) was adjusted to pH 8.0 using 1.5M Tris Base with 0.2M Histidine and 50 mM Arg and 4% PVP K-15

(pH 11) and incubated at 37° C. for 3 hours. Alternately, the pool(s) could be incubated at room temperature for 48 hours.

200 mM reduced glutathione (GSH) in 0.2 M Histidine, 4% PVP, 50 mM Arginine; final pH 8.0, was added until the GSH:Ab ratio was 200× (ex: add 6.88 µL of the glutathione solution for each mg of half-antibody). If the half-antibody pools had not been combined they were combined at this point.

The pooled half-antibodies were incubated at 37° C. for 4 hours to allow for the formation of the bispecific antibody. At this point, the percent bispecific antibody has plateaued.

Once the amount of bispecific antibody has plateaued the solution can be stored at low temperature or adjusted to a lower pH for processing on subsequent chromatography steps.

The methods disclosed herein find use in the manufacture of therapeutic proteins such as bispecific antibodies.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing a heteromultimeric protein, said method comprising:
    a. obtaining a first half-antibody, wherein the first half-antibody comprises a heterodimerization domain;
    b. obtaining a second half-antibody, wherein the second half-antibody comprises a heterodimerization domain;
    c. adjusting pH of each half-antibody to between pH 4 and 9;
    d. mixing the first and second half-antibodies to obtain an assembly mixture;
    e. adding a 50-400x molar excess of glutathione (GSH) to the assembly mixture; and
    f. incubating the assembly mixture to form a heteromultimeric protein comprising the first half-antibody and the second half-antibody.

2. The method of claim 1, wherein the first and second half-antibodies each comprise an Fc component.

3. The method of claim 1, wherein in step c the pH of the first and second half-antibodies are adjusted to pH 4-9 in the presence of a solubilizer.

4. The method of claim 3, wherein the solubilizer is arginine that is added to a final concentration of between 20 mM to 1M prior to adjusting the pH.

5. The method of claim 1, wherein the heterodimerization domain of the first and/or second half-antibodies comprises one or more of a knob, a hole, a leucine zipper, a coiled coil, or a polar amino acid residue capable of forming an electrostatic interaction.

6. The method of claim 1, wherein the heterodimerization domain of the first half-antibody comprises a knob and the heterodimerization domain of the second half-antibody comprises a hole.

7. The method of claim 1, wherein the pH is adjusted after mixing.

8. The method of claim 1, further comprising incubating the assembly mixture at a temperature of between 15° C. and 39° C. for at least 30 minutes.

9. The method of claim 1, wherein the assembly mixture in step f has an oxidation potential of between −200 to −600 mV.

10. The method of claim 1, wherein incubating the assembly mixture is done at a temperature between 15° C. and 39° C. in the presence of Polyvinylpyrrolidone (PVP).

11. The method of claim 10, wherein the PVP is added up to 40% (w/v).

12. The method of 1, wherein the first or second half-antibody is produced by a bacterial cell, a yeast cell, a baculovirus, or a mammalian cell.

13. The method of claim 1, wherein the first or second half-antibody is produced by a CHO cell.

14. The method of claim 1, wherein the GSH is added in 100-300X molar excess.

15. The method of claim 1, wherein the GSH is added in 200X molar excess.

16. The method of claim 6, wherein the knob comprises a T366W substitution and the hole comprises T366S, L368A, and Y407V substitutions.

17. The method of claim 1, further comprising adjusting the pH after the heteromultimeric protein is formed in step f.

18. The method of claim 17, wherein the pH is lowered after the heteromultimeric protein is formed in step f.

19. The method of claim 1, further comprising adjusting the temperature after the heteromultimeric protein is formed in step f.

20. The method of claim 19, wherein the temperature is lowered after the heteromultimeric protein is formed in step f.

* * * * *